United States Patent
Laufersweiler et al.

(10) Patent No.: US 6,566,357 B1
(45) Date of Patent: May 20, 2003

(54) SPIROCYCLIC-6,7-DIHYDRO-5H-PYRAZOLO[1,2-A]PYRAZOL-1-ONES WHICH CONTROL INFLAMMATORY CYTOKINES

(75) Inventors: Matthew John Laufersweiler, Morrow, OH (US); Michael Philip Clark, Loveland, OH (US); Jane Far-Jine Djung, Mason, OH (US); Adam Golebiowski, Loveland, OH (US); Todd Andrew Brugel, West Chester, OH (US); Biswanath De, Cincinnati, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 10/246,499

(22) Filed: Sep. 18, 2002

Related U.S. Application Data

(60) Provisional application No. 60/323,625, filed on Sep. 20, 2001.

(51) Int. Cl.[7] ................ C07D 401/04; C07D 491/113; C07D 495/10; A61K 31/4162
(52) U.S. Cl. .............. 514/221; 514/248; 514/272; 514/275; 540/543; 540/567; 544/230; 544/235; 544/315; 544/330; 544/331
(58) Field of Search ................ 540/543, 567; 544/230, 235, 315, 330, 331; 514/221, 248, 272, 275; 548/357.5, 363.1

(56) References Cited

U.S. PATENT DOCUMENTS 5,780,394 A * 7/1998 Kruger et al. ............. 504/281

OTHER PUBLICATIONS

Aleman et al., PubMed Abstract (Antivir. Ther. 4(2):109–15), 1999.*
Rasmussen, PubMed Abstract (Dan Med Bull 47(2):94–114), 2000.*
Green et al., PubMed Abstract (Immunol Rev 169:11–22), 1999.*
van Deventer, PubMed Abstract (Intensive Care Med 26 Suppl 1:S98–102), 2000.*
Holzheimer, PubMed Abstract (J Chemother 13 Spec No 1(1):159–72), 2001.*

* cited by examiner

Primary Examiner—Deepak Rao
(74) Attorney, Agent, or Firm—Richard S. Echler, Sr.

(57) ABSTRACT

The present invention relates to compound which are capable of preventing the extracellular release of inflammatory cytokines, said compounds, including all enantiomeric and diasteriomeric forms and pharmaceutically acceptable salts thereof, have the formula:

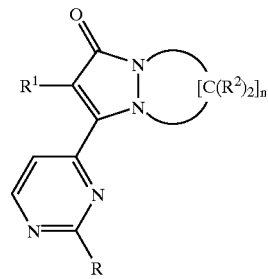

wherein
  R comprises ethers or amines;
  $R^1$ is:
    a) substituted or unsubstituted aryl; or
    b) substituted or unsubstituted heteroaryl;
  two $R^2$ units on the same carbon atom are taken together to form a spirocyclic ring having from 4 to 7 atoms, the balance of the $R^2$ units are independently selected from the group consisting of:
    a) hydrogen;
    b) $-O(CH_2)_j R^8$;
    c) $-(CH_2)_j NR^{9a} R^{9b}$;
    d) $-(CH_2)_j CO_2 R^{10}$;
    e) $-(CH_2)_j OCO_2 R^{10}$;
    f) $-CH_2)_j CON(R^{10})_2$; and
    g) two $R^2$ units can be taken together to form a carbonyl unit;
  $R^8$, $R^{9a}$, $R^{9b}$, and $R^{10}$ are each independently hydrogen, $C_1$–$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5; the index n is from 3 to 5.

28 Claims, No Drawings

SPIROCYCLIC-6,7-DIHYDRO-5H-PYRAZOLO[1,2-A]PYRAZOL-1-ONES WHICH CONTROL INFLAMMATORY CYTOKINES

CROSS REFERENCE TO RELATED APPLICATIONS

This application claims priority under Title 35, United States Code 119(e) from Provisional Application Ser. No. 60/323,625, filed Sep. 20, 2001.

FIELD OF THE INVENTION

The present invention relates to spiro[6,7-dihydro-5H-pyrazolo[1,2a]pyrazol-1-ones] which inhibit the extracellular release of inflammatory cytokines, said cytokines responsible for one or more human or higher mammalian disease states. The present invention further relates to compositions comprising said 6,7-dihydro-5H-pyrazolo[1,2a]pyrazol-1-ones and method for preventing, abating, or otherwise controlling enzymes which are understood to be the active components responsible for the herein described disease states.

BACKGROUND OF THE INVENTION

Interleukin-1 (IL-1) and Tumor Necrosis Factor-α (TNF-α) are among the important biological substances known collectively as "cytokines." These molecules are understood to mediate the inflammatory response associated with the immunological recognition of infectious agents.

These pro-inflammatory cytokines are suggested as an important mediators in many disease states or syndromes, inter alia, rheumatoid arthritis, osteoarthritis, inflammatory bowel disease (IBS), septic shock, cardiopulmonary dysfunction, acute respiratory disease, cachexia, and therefore responsible for the progression and manifestation of human disease states.

There is therefore a long felt need for compounds and pharmaceutical compositions which comprise compounds, which can block, abate, control, mitigate, or prevent the release of cytokines from cells which produce them.

SUMMARY OF THE INVENTION

The present invention meets the aforementioned needs in that it has been surprisingly found that certain spiro-bicyclic pyrazolones and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The first aspect of the present invention relates to compounds, including all enantiomeric and diastereomeric forms and pharmaceutically acceptable salts thereof, said compounds having the formula:

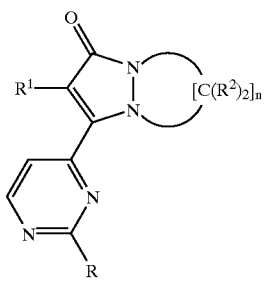

wherein R is:
  a) —O[CH$_2$]$_k$R$^3$; or
  b) —NR$^{4a}$R$^{4b}$;
    R$^3$ is substituted or unsubstituted C$_1$–C$_4$ alkyl, substituted or unsubstituted hydrocarbyl, substituted or unsubstituted heterocyclyl, substituted or unsubstituted aryl or alkylenearyl, substituted or unsubstituted heteroaryl or alkyleneheteroaryl; the index k is from 0 to 5;
    R$^{4a}$ and R$^{4b}$ are each independently:
      a) hydrogen; or
      b) —[C(R$^{5a}$R$^{5b}$)$_2$]$_m$R$^6$;
        each R$^{5a}$ and R$^{5b}$ are independently hydrogen, —OR$^7$, —N(R$^7$)$_2$, —CO$_2$R$^7$, —CON(R$^7$)$_2$; C$_1$–C$_4$ linear, branched, or cyclic alkyl, and mixtures thereof; R$^6$ is hydrogen, R$^7$, —N(R$^7$)$_2$, —CO$_2$R$^7$, —CON(R$^7$)$_2$; substituted or unsubstituted C$_1$–C$_4$ alkyl, substituted or unsubstituted aryl, or substituted or unsubstituted heteroaryl; R$^7$ is hydrogen, a water-soluble cation, or C$_1$–C$_4$ alkyl; the index m is from 0 to 5;
R$^1$ is:
  a) substituted or unsubstituted aryl; or
  b) substituted or unsubstituted heteroaryl;
at least two R$^2$ units of one —[C(R$^2$)$_2$]— ring unit are taken together to form a spirocyclic ring having from 4 to 7 atoms, the balance of the R$^2$ units are independently selected from the group consisting of:
  a) hydrogen;
  b) —(CH$_2$)$_k$O(CH$_2$)$_j$R$^8$;
  c) —(CH$_2$)$_j$NR$^{9a}$R$^{9b}$;
  d) —(CH$_2$)$_j$CO$_2$R$^{10}$;
  e) —(CH$_2$)$_j$OCO$_2$R$^{10}$
  f) —(CH$_2$)$_j$CON(R$^{10}$)$_2$; and
  g) two R$^2$ units can be taken together to form a carbonyl unit;
    R$^8$, R$^{9a}$, R$^{9b}$, and R$^{10}$ are each independently hydrogen, C$_1$–C$_4$ alkyl, and mixtures thereof; R$^{9a}$ and R$^{9b}$ can be taken together to form a carbocyclic or heterocyclic ring comprising from 3 to 7 atoms; two R$^{10}$ units can be take together to form a carbocyclic or heterocyclic ring comprising from 3 to 7 atoms; j is an index from 0 to 5; the index k is from 0 to 5; the index n is from 3 to 5.

Another aspect of the present invention relates to pharmaceutical compositions which can deliver the compounds of the present invention to a human or higher mammal, said compositions comprising:
  a) an effective amount of one or more of the compounds according to the present invention; and
  b) one or more pharmaceutically acceptable excipients.

A further aspect of the present invention relates to methods for controlling one or more inflammatory cytokine mediated or inflammatory cytokine modulated mammalian diseases or conditions, said method comprising the step of administering to a human or higher mammal and effective amount of a composition comprising one or more of the compounds according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (°C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to compounds which are capable of mediating, controlling or otherwise inhibiting the extracellular release of certain cytokines, especially inflammatory cytokines, said cytokines playing a role in the stimulation, cause or manifestation of a wide variety of diseases, disease states, or syndromes.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include pentyl, 3-ethyloctanyl, 1,3-dimethylphenyl, cyclohexyl, cis-3-hexyl, 7,7-dimethylbicyclo[2.2.1]-heptan-1-yl, and naphth-2-yl.

Included within the definition of "hydrocarbyl" are the aromatic (aryl) and non-aromatic carbocyclic rings, non-limiting examples of which include cyclopropyl, cyclobutanyl, cyclopentanyl, cyclohexane, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

The term "heterocycle" includes both aromatic (heteroaryl) and non-aromatic heterocyclic rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

An example of a unit defined by the term "alkylenearyl" is a benzyl unit having the formula:

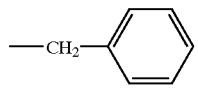

whereas an example of a unit defined by the term "alkyleneheteroaryl" is a 2-picolyl unit having the formula:

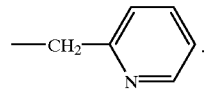

For the purposes of the present invention the terms "spirocyclic" and "spiroannular" are use interchangeably throughout the present specification and are meant to indicate two rings which are conjoined at a single carbon atom, for example:

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. An epoxide unit is an example of a substituted unit which requires replacement of a hydrogen atom on adjacent carbons. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) —[C($R^{12}$)$_2$]$_p$(CH=CH)$_q R^{12}$; wherein p is from 0 to 12; q is from 0 to 12;
ii) —C(Z)$R^{12}$;
iii) —C(Z)$_2 R^{12}$;
iv) —C(Z)CH=CH$_2$;
V) —C(Z)N($R^{12}$)$_2$;
vi) —C(Z)N$R^{12}$N($R^{12}$)$_2$; —vii) —CN;
viii) —CNO;
ix) —CF$_3$, —CCl$_3$, —CBr$_3$;
Z) —N($R^{12}$)$_2$;
xi) —N$R^{12}$CN;
xii) —N$R^{12}$C(Z)$R^{12}$;
xiii) —N$R^{12}$C(Z)N($R^{12}$)$_2$;
xiv) —NHN($R^{12}$)$_2$;
xv) —NHO$R^{12}$;
xvi) —NCS;

xvii) —NO$_2$;
xviii) —OR$^{12}$;
xix) —OCN;
xx) —OCF$_3$, —OCCl$_3$, —OCBr$_3$;
xxi) —F, —Cl, —Br, —I, and mixtures thereof;
xxii) —SCN;
xxiii) —SO$_3$M;
xxiv) —OSO$_3$M;
xxv) —SO$_2$N(R$^{12}$)$_2$;
xxvi) —SO$_2$R$^{12}$;
xxvii) —P(O)H$_2$;
xxviii) —PO$_2$;
xxix) —P(O)(OH)$_2$;
xxx) and mixtures thereof;

wherein R$^{12}$ is hydrogen, substituted or unsubstituted C$_1$–C$_{20}$ linear, branched, or cyclic alkyl, C$_6$–C$_{20}$ aryl, C$_7$–C$_{20}$ alkylenearyl, and mixtures thereof; M is hydrogen, or a salt forming cation; Z is =O, =S, =NR$^{11}$, and mixtures thereof. Suitable salt forming cations include, sodium, lithium, potassium, calcium, magnesium, ammonium, and the like.

The compounds of the present invention comprise a spirocyclic ring scaffold in two parts; the first of which is a 10 to 12 atom fused ring, for example, a 6,7-dihydro-5H-pyrazolo[1,2-a]pyrazol-1-one fused ring system. The second part is a ring comprising from 4 to 7 atoms, said ring attached to the fused ring to form a final spirocyclic ring system.

For the purposes of defining the ring systems of the present invention, the following is provided as an example of the ring numbering system used throughout the present specification to describe the compounds and the variations thereof, which are encompassed by the present invention.

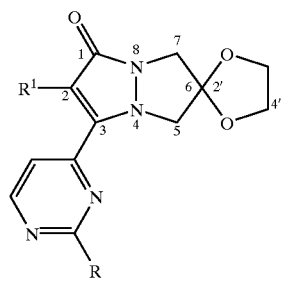

The above scaffold is a spiro[1,3-dioxolane[2',6]-2-R$^1$-substituted-3-[2-R-substituted-pyrimidin-4-yl]-6,7-dihydro-5H-pyrazolo[1,2-a]pyrazol-1-one].

The following is an example of the manner in which the ring systems of the present invention are referred to herein.

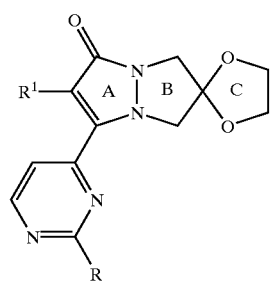

The general definition of the compounds of the present invention have the formula:

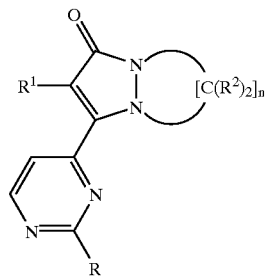

wherein the index n indicates the number of —[C(R$^2$)$_2$]— ring units present and therefore the number of atoms comprising the B-ring of each analog. The "C-ring", which is formed from two R$^2$ units on the same carbon atom, can be formed from any two R$^2$ units from any carbon atom of the B-ring.

The first aspect of the present invention as it relates to ring scaffolds, comprises a 6,7-dihydro-5H-pyrazolo[1,2-a]pyrazol-1-one fused ring system having the formula:

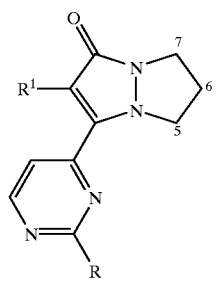

wherein the C-ring can be attached to any of ring positions 5, 6, or 7 as indicated.

The first embodiment of the 6,7-dihydro-5H-pyrazolo[1,2-a]pyrazol-1-one fused ring aspect encompasses spiro[1,3-dioxolane] ring systems having, for example, the formula:

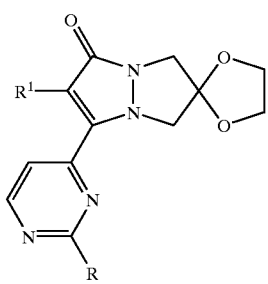

wherein the 1,3-dioxolane ring is attached to the 6-position pyrazolo ring carbon atom. Other iterations of this embodiment include a 1,3-dioxolane ring attached to the 5-position, for example:

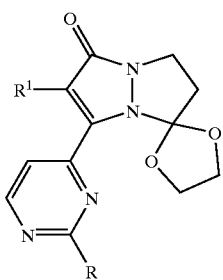

as well as a 1,3-dioxolane ring attached to the 7-position as in the formula:

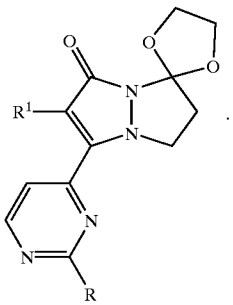

The second embodiment of the 6,7-dihydro-5H-pyrazolo [1,2-a]pyrazol-1-one fused ring. aspect encompasses spiro [1,3-dioxane] ring systems having, for example, the formula:

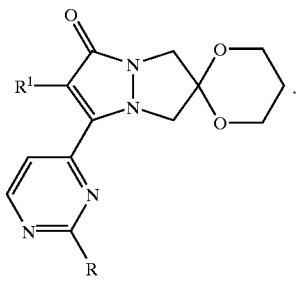

This embodiment also includes iterations wherein the spiro [1,3-dioxane] ring is attached to the 5 and 7 ring positions.

The third embodiment of the 6,7-dihydro-5H-pyrazolo[1, 2-a]pyrazol-1-one fused ring aspect encompasses spiro[1,3-dithiolane] ring systems having, for example, the formula:

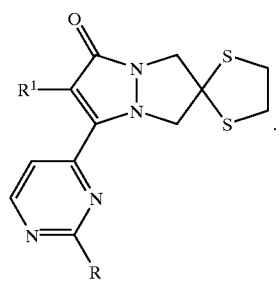

This embodiment also includes iterations wherein the spiro [1,3-dithiolane] ring is attached to the 5 and 7 ring positions.

However, other aspects of the ring systems of the present invention relate to scaffolds having B-rings comprising 6 atoms (n=4) or 7 atoms (n=5) which are exemplified herein below by the formulae:

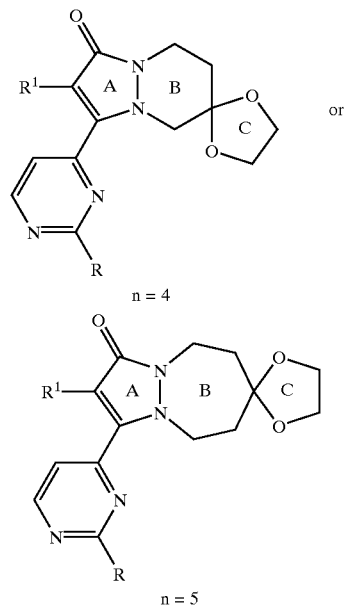

The first ring system in the above two examples comprises, as the fused ring component, a 5,6,7,8-tetrahydro-pyrazolo[1,2-a]pyridazin-1-one system and the second scaffold comprises, as its fused ring component, a 6,7,8,9-tetrahydro-5H-pyrazolo[1,2-a][1,2]diazepin-1-one ring system. Each of these ring systems is a component of separate aspects of the ring scaffolds of the present invention.

Within the metes and bounds of the first aspect as it relates to ring scaffolds, the B-ring comprises 5-atoms and the C-ring is a [1,3]dioxolane, [1,3]dioxane, or [1.3]dithiolane ring as illustrated herein above. The carbon to which said C-ring is attached, for example, any of carbons atoms numbered 5, 6, or 7, relate to the embodiments of this first aspect.

The second aspect of the present invention relates to inflammatory cytokine release inhibitors wherein the index n equals 4, said scaffolds having, for example, the formula:

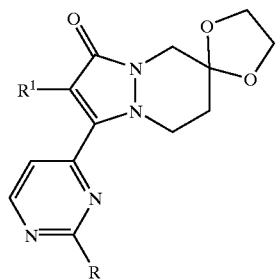

which are spiro[5,6,7,8-tetrahydro-pyrazolo[1,2-a] pyridazin-1-one] ring systems wherein the C-ring may be attached at any of carbon atom ring positions 5, 6, 7, or 8. Within the metes and bounds of the second aspect as it relates to ring scaffolds, the B-ring comprises 6-atoms and the C-ring is a [1,3]dioxolane, [1,3]dioxane, or [1.3] dithiolane ring as illustrated herein above. The carbon to which said C-ring is attached, for example, any of carbons atoms numbered 5, 6, 7, or 8, relate to the embodiments of this second aspect.

The third aspect of the present invention relates to inflammatory cytokine release inhibitors wherein the index n equals 5, said scaffolds having, for example, the formula:

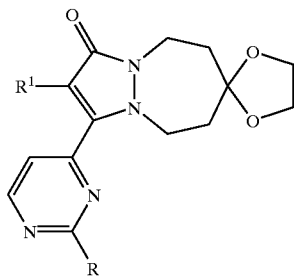

which are spiro[6,7,8,9-tetrahydro-5H-pyrazolo[1,2-a][1,2] diazepin-1-one] ring systems wherein the C-ring may be attached at any of carbon atom ring positions 5, 6, 7, 8, or 9. Within the metes and bounds of the second aspect as it relates to ring scaffolds, the B-ring comprises 7-atoms and the C-ring is a [1,3]dioxolane, [1,3]dioxane, or [1,3] dithiolane ring as illustrated herein above. The carbon to which said C-ring is attached, for example, any of carbons atoms numbered 5, 6, 7, 8, or 9, relate to the embodiments of this third aspect.

The compounds of the present invention comprise a pyrimidine ring attached to the 3-position of the A-ring. R units are substituents at the 2-position of the pyrimidin-4-yl portion of the general scaffold, said R units are:
a) an ether having the formula —O[CH$_2$]$_k$R$^3$; or
b) an amino unit having the formula —NR$^{4a}$R$^{4b}$;
   wherein R$^3$ is substituted or unsubstituted C$_1$–C$_4$ alkyl, substituted or unsubstituted cyclic hydrocarbyl, substituted or unsubstituted heterocyclyl, substituted or unsubstituted aryl or alkylenearyl, substituted or unsubstituted heteroaryl or alkyleneheteroaryl; the index k is from 0 to 5.

The following are the various aspects of R units according to the present invention wherein R is an ether having the formula —O[CH$_2$]$_k$R$^3$.
A) R units encompassing ethers having the formula —OR$^3$ (the index k equal to 0) and R$^3$ is substituted or unsubstituted aryl.
   i) One iteration of this aspect of R comprises ethers having the formula —OR$^3$ and R$^3$ is substituted or unsubstituted aryl. This iteration includes the following non-limiting example of R: phenoxy, 2-fluorophenoxy, 3-fluorophenoxy, 4-fluorophenoxy, 2,4-difluorophenoxy, 3-trifluoromethylphenoxy, 4-trifluoromethylphenoxy, 2,4-trifluoromethyl phenoxy, and the like.
   ii) Another iteration of this aspect of R comprises ethers having the formula —OR$^3$ and R$^3$is substituted or unsubstituted aryl. This iteration includes the following non-limiting examples: 2-methylphenoxy, 3-methylphenoxy, 4-methylphenoxy, 2,4-dimethylphenoxy, 2-cyanophenoxy, 3-cyanophenoxy, 4-cyanophenoxy, 4-ethylphenoxy, and the like.
   iii) A further iteration of this aspect of R comprises ethers having the formula —OR$^3$ and R$^3$is substituted or unsubstituted aryl. This iteration includes the following non-limiting examples: (2-methyoxy)phenoxy, (3-methoxy)phenoxy, (4-methoxy)phenoxy, 3-[(N-acetyl)amino]phenoxy, 3-benzo[1,3]dioxol-5-yl, and the like.
B) R units encompassing ethers having the formula —OR$^3$ (the index k equal to 0) and R$^3$ is substituted or unsubstituted heteroaryl.
   i) A first iteration of this aspect of R comprises ethers having the formula —OR$^3$ and R$^3$ is unsubstituted heteroaryl. This iteration includes the following non-limiting examples: pyrimidin-2-yl, pyrimidin-4-yl, pyridin-2-yl, pyridin-3-yl, pyridin-4-yl, and the like.
   ii) A second iteration of this aspect of R comprises ethers having the formula —OR$^3$ and R$^3$ is substituted heteroaryl. This iteration includes the following non-limiting examples: 2-aminopyrimidin-4-yl, and the like.
C) R units encompassing ethers having the formula —OCH$_2$R$^3$ (the index k equal to 1) and R$^3$ is substituted or unsubstituted aryl.
   i) A first iteration of this aspect of R comprises ethers having the formula —OCH$_2$R$^3$ and R$^3$ is substituted or unsubstituted heteroaryl. This iteration includes the following non-limiting examples: pyrimidin-2-yl, pyrimidin-4-yl, 2-aminopyrimidin-4-yl, 4-aminopyrimidin-6-yl, pyridin-2-yl, pyridin-3-yl, pyridin-4-yl, and the like.
   ii) A second iteration of this aspect of R wherein R is an ether having the formula —OCH$_2$R$^3$ and R$^3$ is substituted or unsubstituted alkylenehetero-aryl. This iteration includes the following non-limiting examples: pyridin-3-ylethyl, (2-methyl-2-pyridin-3-yl)ethyl, and the like.
D) R units encompassing ethers having the formula —OR$^3$ (the index k equal to 1) and R$^3$ is R$^3$ is substituted or unsubstituted C$_1$–C$_4$ alkyl.
   i) A first iteration of this aspect of R is an ether having the formula —OR$^3$ and R$^3$ is unsubstituted C$_1$–C$_4$ linear, branched, or cyclic alkyl. This iteration includes the following non-limiting examples: methyl, ethyl, isopropyl, (S)-1-methypropyl, and the like.
   ii) A second iteration of this aspect of R is an ether having the formula —OR$^3$ and R$^3$ is a substituted C$_1$–C$_4$ linear, branched, or cyclic alkyl. This iteration includes the following non-limiting examples: 2-methoxyethyl, (S)-1-methy-3-methyoxypropyl, and the like.

However, the formulator is not limited to the herein exemplified iterations and examples.

The following are the various aspects of R units according to the present invention wherein R is an amine having the formula —NR$^{4a}$R$^{4b}$, R$^{4a}$ and R$^{4b}$ are each independently:
a) hydrogen; or
b) —[C(R$^{5a}$R$^{5b}$)$_2$]$_m$R$^6$;
   each R$^{5a}$ and R$^{5b}$ are independently hydrogen, C$_1$–C$_4$ linear, branched, or cyclic alkyl, and mixtures thereof; R$^6$ is hydrogen, substituted or unsubstituted C$_1$–C$_4$ alkyl, C$_2$–C$_4$ alkenyl, —OR$^7$, —N(R$^7$)$_2$, —CO$_2$R$^7$, —CON(R$^7$)$_2$, substituted or unsubstituted aryl, or substituted or unsubstituted heteroaryl; R$^7$ is hydrogen, a water-soluble cation, or C$_1$–C$_4$ alkyl; the index m is from 0 to 5.
A) R units encompassing chiral amino groups wherein R$^{4a}$ is hydrogen, R$^{5a}$ is hydrogen and R$^{5b}$ is methyl, said units having the formula:

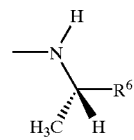

and the indicated stereochemistry.

i) A first iteration of this aspect of R is an amine comprising an $R^6$ which is substituted or unsubstituted phenyl. This iteration includes the following non-limiting examples: (S)-1-methyl-1-phenylmethylamino, (S)-1-methyl-1-(4-fluorophenyl) methylamino, (S)-1-methyl-1-(4-methylphenyl)methyl-amino, (S)-1-methyl-1-(4-methoxyphenyl)methylamino, (S)-1-methyl-1-(2-aminophenyl)methylamino, (S)-1-methyl-1-(4-aminophenyl)methylamino, and the like.

ii) A second iteration of this aspect of R is an amine comprising an $R^6$ which is substituted or unsubstituted heteroaryl. This iteration includes the following non-limiting examples: (S)-1-methyl-1-(pyridin-2-yl)methylamino, (S)-1-methyl-1-(pyridin-3-yl)methylamino, (S)-1-methyl-1-(pyridin-4-yl)methylamino, (S)-1-methyl-1-(furan-2-yl)methylamino, (S)-1-methyl-1-(3-benzo[1,3]dioxol-5-yl)methylamino, and the like.

iii) A third iteration of this aspect of R is an amine comprising an $R^6$ which is $C_1$–$C_4$ substituted or unsubstituted alkyl. This iteration includes the following non-limiting examples: (S)-1-methylpropylamino, (S)-1-methyl-2-(methoxy)ethylamino.

B) R units encompassing chiral amino groups wherein $R^{4a}$ is hydrogen, $R^{5a}$ and $R^{5b}$ are each $C_1$–$C_4$ alkyl, said units having the formula:

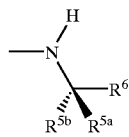

and the indicated stereochemistry when $R^{5a}$, $R^{5b}$ and $R^6$ are not the same.

i) A first iteration of this aspect of R is an amine which does not have a chiral center, non-limiting examples of which includes 1,1-dimethylethylamine, 1,1-dimethylbenzylamine and the like.

ii) A second iteration of this aspect of R is an amine comprising an $R^6$ which is substituted or unsubstituted $C_1$–$C_4$ alkyl. This iteration includes the following non-limiting examples: (S)-1-methyl-2-hydroxy-2-methylpropylamine, (S)-1-methyl-2-hydroxy-2-methylbutylamine, and the like.

C) R units encompassing alkylenearyl amines wherein $R^{4a}$ is hydrogen, both $R^{5a}$ and $R^{5b}$ of $R^{4b}$ are hydrogen, $R^6$ is substituted or unsubstituted aryl, said unit having the formula:

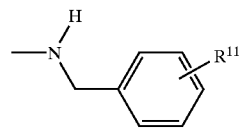

wherein $R^{11}$ is hydrogen or a "substituted unit" as defined herein above.

i) A first iteration of this aspect comprises the following non-limiting examples of R units: benzylamino, (2-aminophenyl)methylamino; (4-fluorophenyl)methylamino, (4-methoxyphenyl)methylamino; (4-propanesulfonylphenyl)methylamino, and the like.

ii) A second iteration of this aspect comprises the following non-limiting examples of R units: (2-methylphenyl)methylamino; (3-methylphenyl)-methylamino; (4-methylphenyl)methylamino; and the like.

D) R units encompassing amines wherein $R^{4a}$ is hydrogen, $R^{4b}$ comprises $R^{5a}$ equal to hydrogen and $R^{5b}$ equal to —$CO_2R^7$ or —$CON(R^7)_2$; said unit having the formula:

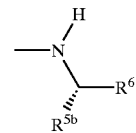

i) A first iteration of this aspect of R is an amine comprising an $R^6$ which is substituted or unsubstituted phenyl. This iteration includes the following non-limiting examples:

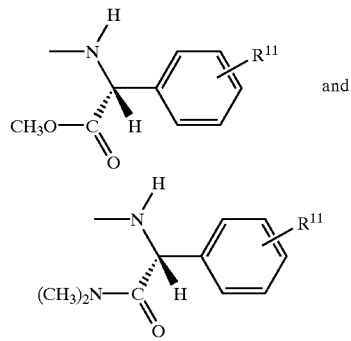

wherein $R^{11}$ is hydrogen or a "substitute" as defined herein above.

ii) A second iteration of this aspect of R is an amine comprising an $R^6$ which is substituted or unsubstituted alkyl. This iteration includes the following non-limiting examples:

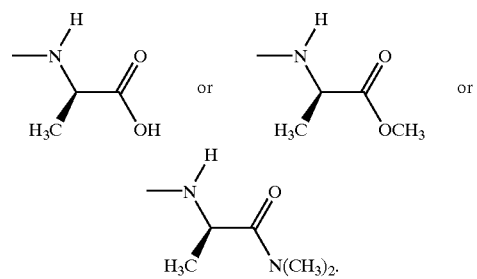

However, the formulator is not limited to the herein exemplified iterations and examples.

$R^1$ units are selected from:
a) substituted or unsubstituted aryl; or
b) substituted or unsubstituted heteroaryl.

The first aspect of $R^1$ units encompasses halogen substituted phenyl units, non-limiting examples of which include 4-fluorophenyl, 2,4-difluorophenyl, 4-chlorophenyl, and the like.

$R^2$ units comprise the spiroannular ring of the scaffold of the present invention. In addition, $R^2$ units comprise the substituted or unsubstituted methylene units having the formula —$[C(R^2)_2]$—. When $R^2$ units are not a part of the 5–7 atom spirocyclic ring portion of the scaffold, each $R^2$ unit is independently selected from the group consisting of:
  a) hydrogen;
  b) $-(CH_2)_k O(CH_2)_j R^8$;
  c) $-(CH_2)_j NR^{9a}R^{9b}$;
  d) $-(CH_2)_j CO_2 R^{10}$;
  e) $-(CH_2)_j OCO_2 R^{10}$;
  f) $CH_2)_j CON(R^{10})_2$;
  g) two $R^2$ units can be taken together to form a carbonyl unit;
  h) and mixtures thereof;
   $R^8$, $R^{9a}$, $R^{9b}$, and $R^{10}$ are each independently hydrogen, $C_1$–$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5; n is an index from 3 to 5.

As described herein above the value of the index n indicates the size of the "B-ring". The first aspect of the scaffolds of the present invention relates to B-rings wherein n is equal to 3, for example, compounds comprising the 6,7-dihydro-5H-pyrazolo[1,2-a)pyrazol-1-one ring system non-limiting examples of which include:

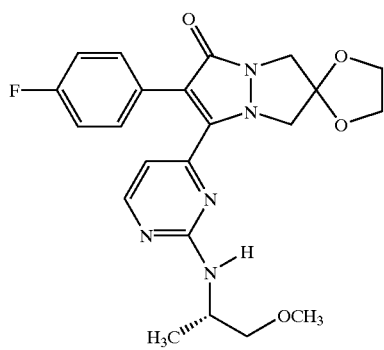

spiro[1,3-dioxolane[2',6]-2-(4-fluorophenyl)-3-{2-(S)-[(2-methoxy-1-methyl)ethylamino]-pyrimidin-4-yl}-6,7-dihydro-5H-pyrazolo[1,2-a]pyrazol-1-one]; and

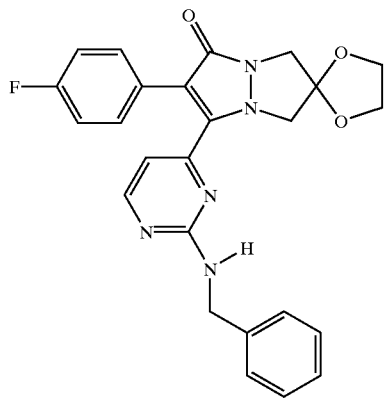

spiro[1,3-dioxolane[2',6]-2-(4-fluorophenyl)-3-[2-(benzylamino)pyrimidin-4-yl]]-6,7-dihydro-5H-pyrazolo[1,2-a]pyrazol-1-one].

A second embodiment of the first aspect relates to pyrazolo[1,2-a]pyrazol-1-one ring systems comprising a spiro[1,3-doxoxane], non-limiting examples of which include:

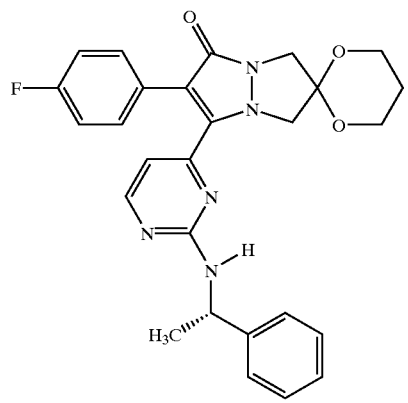

spiro[1,3-dioxane[2',6]-2-(4-fluorophenyl)-3-{2-(S)-[(α-methyl)benzylamino]-pyrimidin-4-yl}-6,7-dihydro-5H-pyrazolo[1,2-a]pyrazol-1-one]; and

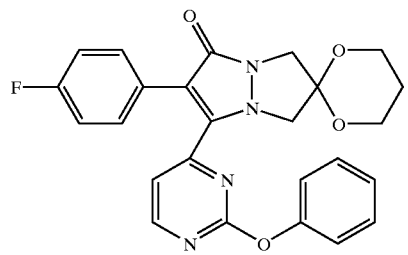

spiro[1,3-dioxolane[2',6]-2-(4-fluorophenyl)-3-[2-(phenoxy)pyrimidin-4-yl]-6,7-dihydro-5H-pyrazolo[1,2-a]pyrazol-1-one].

The compounds, which comprise the inflammatory cytokine release inhibiting analogs of the present invention are divided into several non-limiting categories. Several of the analog categories are set forth as follows.

The first aspect of Category I inflammatory cytokine release inhibiting compounds according to the present invention have the general scaffold having the formula:

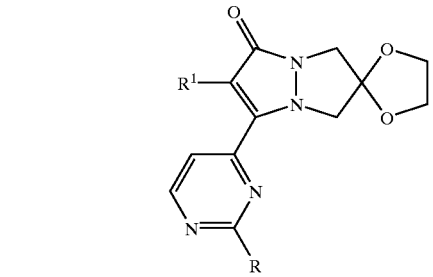

which are 2',6-spiro[1,3-dioxolane] derivatives of 6,7-dihydro-5H-pyrazolo[1,2-a]pyrazol-1-ones wherein R units have the formula:

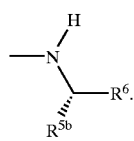

Table I here below provides non-limiting examples of $R^1$, $R^{5b}$, and $R^6$.

TABLE I

| No. | R¹ | R⁵ᵇ | R⁶ |
|---|---|---|---|
| 1 | 4-fluorophenyl | methyl | methyl |
| 2 | 4-fluorophenyl | methyl | ethyl |
| 3 | 4-fluorophenyl | methyl | propyl |
| 4 | 4-fluorophenyl | methyl | vinyl |
| 5 | 4-fluorophenyl | methyl | cyclopropyl |
| 6 | 4-fluorophenyl | methyl | cyclohexyl |
| 7 | 4-fluorophenyl | methyl | methoxymethyl |
| 8 | 4-fluorophenyl | methyl | methoxyethyl |
| 9 | 4-fluorophenyl | methyl | 1-hydroxy-1-methylethyl |
| 10 | 4-fluorophenyl | methyl | —CO₂H |
| 11 | 4-fluorophenyl | methyl | phenyl |
| 12 | 4-fluorophenyl | methyl | 4-fluorophenyl |
| 13 | 4-fluorophenyl | methyl | 2-aminophenyl |
| 14 | 4-fluorophenyl | methyl | 2-methylphenyl |
| 15 | 4-fluorophenyl | methyl | 4-methylphenyl |
| 16 | 4-fluorophenyl | methyl | 4-methoxyphenyl |
| 17 | 4-fluorophenyl | methyl | 4-(propanesulfonyl)phenyl |
| 18 | 4-fluorophenyl | methyl | 3-benzo[1,3]dioxol-5-yl |
| 19 | 4-fluorophenyl | methyl | pyridin-2-yl |
| 20 | 4-fluorophenyl | methyl | pyridin-3-yl |

The second aspect of Category I inflammatory cytokine release inhibiting compounds according to the present invention comprise the general scaffold having the formula:

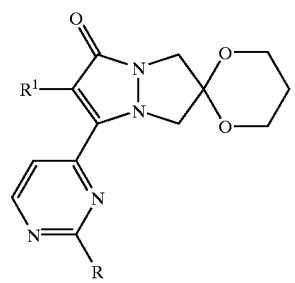

which are 2',6-spiro[1,3-dioxane] derivatives of 6,7-dihydro-5H-pyrazolo[1,2-a]pyrazol-1-ones. The first aspect of Category I relates to compounds wherein R units have the formula:

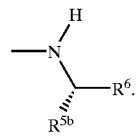

Table II herein below provides non-limiting examples of $R^1$, $R^{5b}$, and $R^6$.

TABLE II

| No. | R¹ | R⁵ᵇ | R⁶ |
|---|---|---|---|
| 21 | 4-fluorophenyl | methyl | methyl |
| 22 | 4-fluorophenyl | methyl | ethyl |
| 23 | 4-fluorophenyl | methyl | propyl |
| 24 | 4-fluorophenyl | methyl | vinyl |
| 25 | 4-fluorophenyl | methyl | cyclopropyl |
| 26 | 4-fluorophenyl | methyl | cyclohexyl |
| 27 | 4-fluorophenyl | methyl | methoxymethyl |
| 28 | 4-fluorophenyl | methyl | methoxyethyl |
| 29 | 4-fluorophenyl | methyl | 1-hydroxy-1-methylethyl |
| 30 | 4-fluorophenyl | methyl | —CO₂H |
| 31 | 4-fluorophenyl | methyl | phenyl |
| 32 | 4-fluorophenyl | methyl | 4-fluorophenyl |
| 33 | 4-fluorophenyl | methyl | 2-aminophenyl |
| 34 | 4-fluorophenyl | methyl | 2-methylphenyl |
| 35 | 4-fluorophenyl | methyl | 4-methylphenyl |
| 36 | 4-fluorophenyl | methyl | 4-methoxyphenyl |
| 37 | 4-fluorophenyl | methyl | 4-(propanesulfonyl)phenyl |
| 38 | 4-fluorophenyl | methyl | 3-benzo[1,3]dioxol-5-yl |
| 39 | 4-fluorophenyl | methyl | pyridin-2-yl |
| 40 | 4-fluorophenyl | methyl | pyridin-3-yl |

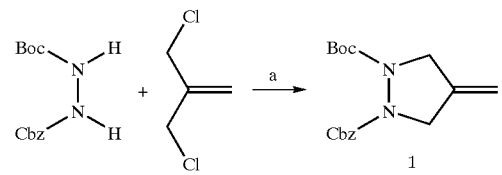

Reagents and conditions: (a) NaH

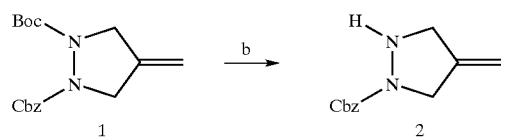

Reagents and Conditions: (b) SOCl₂, MeOH

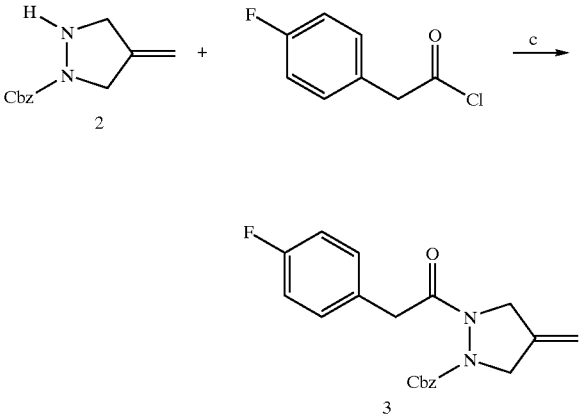

Reagents and Conditions: (c) NaOH, CH₂Cl₂/water, rt 18 hours.

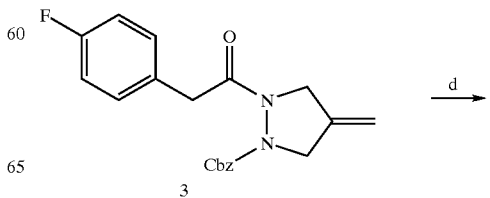

-continued
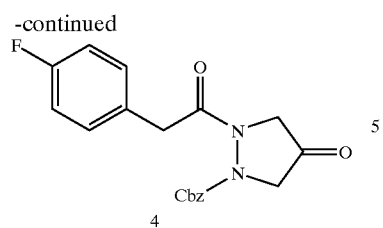
4
Reagents and Conditions: (d) O₃, CH₂Cl₂, DMS; −78° C. to rt 18 hr.
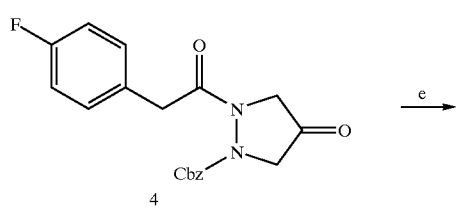
4
Reagents and Conditions: (e) ethylene glycol, TsOH, toluene, reflux 18 hr.
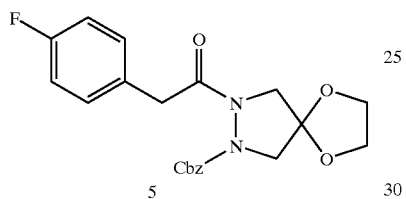
5
Reagents and Conditions: (f) H₂: Pd/C, MeOH; rt 4 hr.
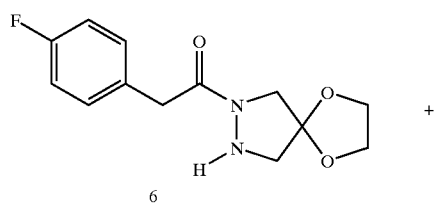
6
+
-continued
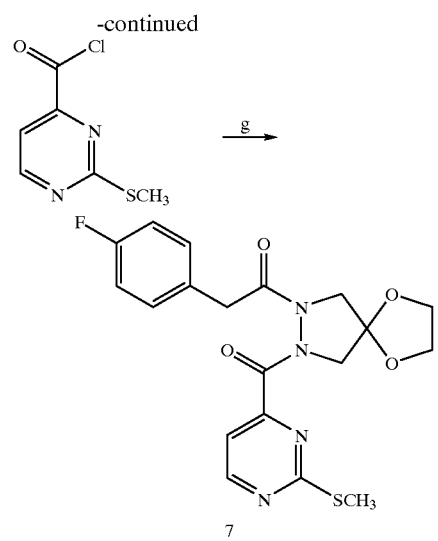
7
Reagents and Conditions: (g) NaOH: CH₂Cl₂/water, rt 12 hr.
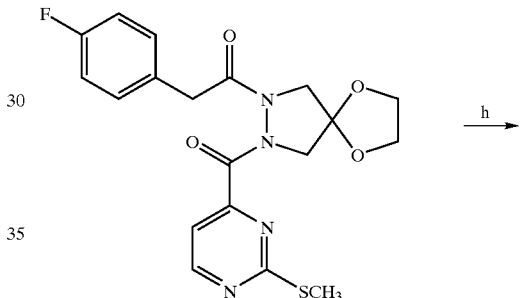
8
Reagents and Conditions: (h) NaH, DMF; 0° C. to rt, 3 hr.
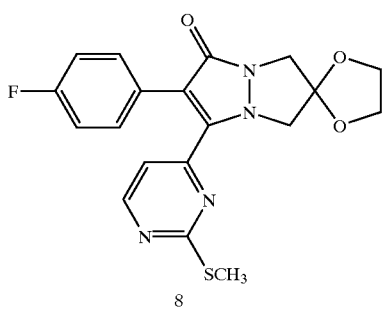
8

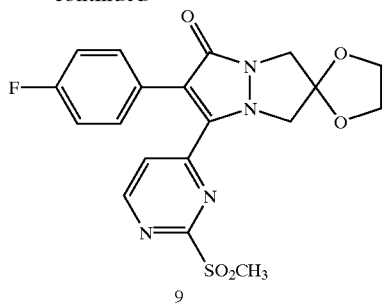

Reagents and Conditions: (i) Oxone®, MeOH/THF/ H₂O; rt 2 hr.

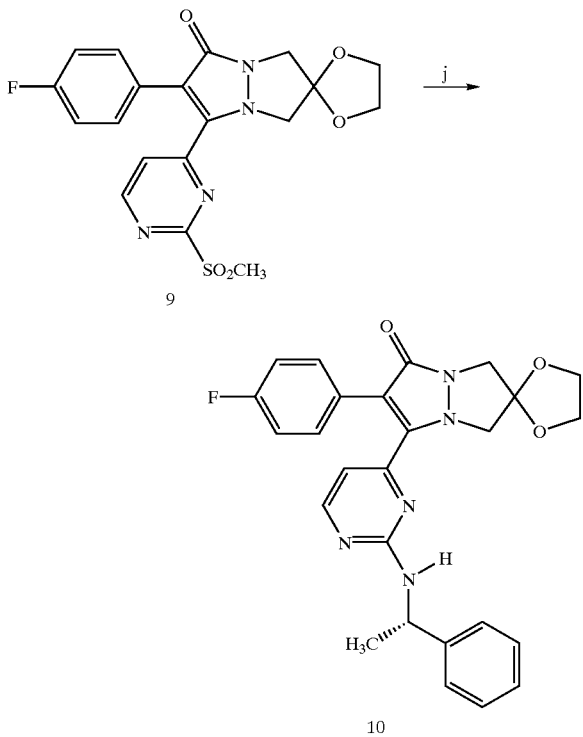

Reagents and Conditions: (j) (α)-(−)-methylbenzylamine, 100° C. 3 hr.

EXAMPLE 1

Spiro[1,3-dioxolane[2',6]-2-[2-(4-fluorophenyl) acetyl]-3-[2-(1-phenylethylamino)pyrimidin-4-yl]-6, 7-dihydro-5H-pyrazolo[1,2-a]pyrazol-1-one] (10)

Preparation of 4-methylenepyrazolidine-1,2-dicarboxylic acid 1-benzyl ester 2-tert-butyl ester (1): To a suspension of NaH (3.81 g, 95.4 mmol) in DMF (80 mL) is add dropwise a solution of N-Cbz-N'-Boc-hydrazine (12.1 g, 45.4 mmol) in DMF (20 mL). The reaction mixture is stirred about 20 minutes and 3-chloro-2-chloromethyl-propene ( 5.8 mL, 50 mmol) is added dropwise and the reaction is allowed to stir at room temperature unit the reaction is complete by TLC. The reaction solution is partitioned between ethyl acetate and water, the water layer being extracted several times more with solvent. The combined organic layers are dried, filtered, and concentrated to afford the desired product as a clear oil which is used without further purification.

Preparation of 4-methylene-pyrazolidine-1-carboxylic acid 1-benzyl ester (2): To a solution of crude 4-methylenepyrazolidine-1,2-dicarboxylic acid 1-benzyl ester 2-tert-butyl ester, 1, (30 g) in methanol (300 mL) is added thionyl chloride dropwise at 0° C. The reaction is warmed to room temperature and stirred an additional 18 hours. Concentration of the reaction in vacuo affords a yellow oil which crystallizes upon standing to provide 23 g (97% yield) of the desired product as the HCl salt.

Preparation of 2-[2-(4-fluorophenyl)acetyl]-4-methylene-pyrazolidine-1-carboxylic acid benzyl ester (3): Sodium hydroxide (0.12 g, 3 mmol) is dissolved in a 1:2 water/ methylene chloride solution (30 mL) with rapid stirring followed by the addition of 4-methylene-pyrazolidine-1-carboxylic acid 1-benzyl ester, 2, (0.62 g, 2.8 mmol) at room temperature. (4-Fluorophenyl)acetyl chloride (0.39 mL, 4.2 mmol) is added and the reaction is allowed to stir for 18 hours after which time the reaction mixture is diluted with water (10 mL) and the layers allowed to separate. The aqueous layer is extracted with methylene chloride, the organic layers combined, dried, and filtered. Concentration in vacuo affords the crude product which is purified over silica (1:3 ethyl acetate/hexane) to provide 0.54 g (62% yield) of the desired product.

Preparation of 2-[2-(4-fluorophenyl)acetyl]-4-oxo-pyrazolidine-1-carboxylic acid benzyl ester (4): Ozone gas is bubbled into a solution of 2-[2-(4-fluorophenyl)-acetyl] 4-methylene-pyrazolidine-1-carboxylic acid benzyl ester, 3, (0.28 g, 0.8 mmol) in methylene chloride (15 mL) at −78° C. until the solution retains a blue color. The source of ozone is removed and dimethyl sulfoxide (0.23 mL) is added and the reaction solution allowed to warm to room temperature and stir for 18 hours. The solvent is removed in vacuo and the resulting oil purified over silica (1:3 ethyl acetate/ hexane) to afford 0.15 g (53% yield) of the desired product as a clear oil.

Preparation of spiro[1,3-dioxolane[2',4]-2-[2-(4-fluorophenyl)acetyl]-pyrazolidine-1-carboxylic acid benzyl ester] (5): To a flask fitted with a Dean-Stark trap is charged 2-[2-(4-fluorophenyl)acetyl]4-oxo-pyrazolidine-1-carboxylic acid benzyl ester, 4, (4.0 g, 11.2 mmol), ethylene glycol (6.26 mL, 112 mmol), toluenesulfonic acid (400 mg), and toluene (40 mL). The mixture is heated to reflux for 3 days, then concentrated in vacuo to a brown oil which is taken up in CH₂Cl₂, washed with NaHCO₃, dried and concentrated to a brown oil. The crude product obtained is purified over silica (ethyl acetate/hexane 1:3) to afford 2.68 g (59.7% yield) of the desired product.

Preparation of spiro[1,3-dioxolane[2',6]-2-(4-fluorophenyl)-1-pyrazolidin-1-yl-ethanone (6): Spiro[1,3-dioxolane[2',4]-2-[2-(4-fluorophenyl)acetyl]-pyrazolidine-1-carboxylic acid benzyl ester], 5, (400 mg, 1 mmol) is dissolved in methanol and Pd/C (40 mg) is added. The solution is then hydrogenated of a Parr® Hydrogenation Apparatus for 4 hours after which time the catalyst is removed by filtration and the filtrate concentrated in vacuo to afford 265 mg (99% yield) of the desired product as a pale tan solid.

Preparation of spiro[1,3-dioxolane[2',6]-2-(4-fluorophenyl)-1-[2-(2-methylsulfanyl-pyrimidine-4-carbonyl)-pyrazolidin-1-yl]-ethanone] (7): To a solution of spiro[1,3-dioxolane[2',6]-2-(4-fluorophenyl)-1-pyrazolidin-1-yl-ethanone, 6, (265 mg, 1 mmol) in dichloromethane (2 mL) is added 2-methylsulfonyl-pyrimidine4-carbonyl chloride (375 mg, 2 mmol) followed by dropwise addition of a 1.0 N aqueous solution of sodium hydroxide (3.5 mL). The mixture is vigorously stirred at room temperature for 3 days. The reaction is diluted with dichloromethane (10 mL) and washed with water (10 mL). The aqueous layer is back-extracted with dichloromethane (10 mL). The combined organic layers are washed with a saturated aqueous solution of sodium bicarbonate (10 mL) and brine (10 mL), dried, filtered and concentrated in vacuo. The resulting crude material is purified over silica (1:1 hexane/ethyl acetate to 100% ethyl acetate) to afford 314 mg (75% yield) of the desired product as a clear oil.

Preparation of spiro[1,3-dioxolane[2',6]-2-(4-fluorophenyl)-3-(2-methylsulfanyl-pyrimidin-4-yl)-6,7-dihydro-5H-pyrazolo[1,2-a]pyrazol-1-one] (8): Spiro[1,3-dioxolane[2',6]-2-(4-fluorophenyl)-1-[2-(2-methylsulfanyl-pyrimidine-4-carbonyl)-pyrazolidin-1-yl]-ethanone], 7, (314 mg, 0.75 mmol) is dissolved in THF (5 mL). This solution is then added dropwise via cannula to a suspension of NaH (45 mg of a 60% dispersion in mineral oil, 1.1 mmol) at 0° C. The reaction is allowed to gradually warm to room temperature then the THF is removed in vacuo. The resulting residue is dissolved in dichloromethane and washed with water. The aqueous layer is back-extracted with more solvent, the organic layers are combined, dried and concentrated in vacuo to provide the crude product which is purified over silica (100% ethyl acetate to 5% to 10% to 20% methyl alcohol/ethyl acetate) to afford 44 mg (19.6% yield) of the desired product as a yellow solid.

Preparation of spiro[1,3-dioxolane[2',6]-2-(4-fluorophenyl)-3-(2-metanesulfonyl-pyrimidin-4-yl)-6,7-dihydro-5H-pyrazolo[1,2-a]pyrazol-1-one] (9): To a solution of spiro[1,3-dioxolane[2',6]-2-(4-fluorophenyl)-3-(2-methylsulfanyl-pyrimidin-4-yl)-6,7-dihydro-5H-pyrazolol[1,2-a]pyrazol-1-one], 8, (44 mg, 0.1 mmol) in THF:methanol/water (5 mL of a 2:1:2 mixture) is added dropwise a solution of Oxone® (potassium peroxymonosulfate) (270 mg, 0.4 mmol) in water. The reaction is allowed to warm to room temperature, partitioned between $CH_2Cl_2$ and water, the aqueous layer re-extracted with solvent, after which the organic layers are combined, dried, and concentrated in vacuo to afford 45 mg (95% yield) of the crude desired product which is a mixture of the sulfoxide and sulfone and which is used without further purification.

Preparation of spiro[1,3-dioxolane[2',6]-2-(4-fluorophenyl)-3-[(2-(S)-(α)-methyl-benzylamino)pyrimidin-4-yl]-6,7-dihydro-5H-pyrazolo[1,2-a-]pyrazol-1-one] (10): A solution of the crude spiro[1,3-dioxolane[2',6]-2-(4-fluorophenyl)-3-(2-metanesulfonyl-pyrimidin-4-yl)-6,7-dihydro-5H-pyrazolo[1,2-a]pyrazol-1-one], 9, prepared as described herein above (100 mg, 0.23 mmol) and (S)-(–)-α-methyl-benzyl amine (2 mL) are dissolved in toluene (2 mL). The resulting mixture is heated to 100° C. for 3 hours, cooled to room temperature and the solvent removed in vacuo. The resulting residue is purified over silica (1:1 EtOAc/hexanes) to afford 77 mg (70% yield) of the desired product as a yellow solid. $^1H$ NMR (CDCl$_3$, 300 MHz) δ 1.60 (d, 3 H, J=6.9 Hz), 3.92–4.09 (m, 8 H), 5.15 (q, 1 H, J=5.1, 6.9 Hz), 5.67 (d, 1 H, J=5.1 Hz), 6.41 (d, 1 H, J=5.1 Hz), 7.01–7.07 (m, 2 H), 7.26–7.43 (m, 7 H), 8.18 (d, 1 H, J=5.1 Hz). ESI$^-$ MS: m/z (rel intensity) 474.27 (100, M$^+$+H). Anal. Calculated for $C_{26}H_{24}FN_5O_3$ 0.25$H_2O$: C, 65.33; H, 5.17; N, 14.65. Found: C, 65.22; H, 4.58; N, 14.19.

Spiro[1,3-dioxolane[2',6]-2-(4-fluorophenyl)-3-[2-(1-(S)-methyl-2-methoxyethylamino)pyrimidin-4-yl]4,7-dihydro-5H-pyrazolo[1,2-a]pyrazol-1-one]: $^1H$ NMR (CDCl$_3$, 300 MHz) δ 1.31 (d, 3 H, J=6.6 Hz), 3.42 (s, 3 H), 3.48 (d, 3 H, J=4.8 Hz), 4.07–4.11 (m, 6 H), 4.16 (d, 2H, J=3.6 Hz), 4.20–4.30 (m, 1 H), 6.44 (d, 1 H, J=5.1 Hz), 7.04–7.10 (m, 2 H), 7.41–7.46 (m, 2H ), 8.15 (d, 1 H, J=5.1 Hz). ESI$^-$ MS: m/z (rel intensity) 442.25 (100, M$^+$+H) Anal. Calculated for $C_{22}H_{24}FN_5O_4$ 0.25$H_2O$: C, 59.25; H, 5.54; N, 15.70. Found: C, 59.37; H, 5.17; N, 15.52.

Spiro[1,3-dioxolane[2',6]-2-(4-fluorophenyl)-3-[2-(benzylamino)pyrimidin-4-yl]6,7-dihydro-5H-pyrazolo[1,2-a]pyrazol-1-one]: $^1H$ NMR (CDCl$_3$, 300 MHz) δ 3.61–3.86 (m, 8 H), 4.51 (d, 2 H, J=5.89 Hz), 6.29 (d, 1 H, J=5.2 Hz), 6.87–7.09 (m, 2 H), 7.11–7.25 (m, 7 H), 7.99 (d, 1 H, J=5.2 Hz). HRMS: m/z (rel. intensity) $C_{25}H_{22}FN_5O_3$ Calc. 460.1785 (M$^+$+H), found 460.1775.

Spiro[1,3-dioxolane[2',6]-2-(4-fluorophenyl)-3-[2-(1-(S)-methyl-2-hydroxy-2-methylpropyl-amino)pyrimidin-4-yl]-6,7-dihydro-5H-pyrazolo[1,2-a]pyrazol-1-one]: $^1H$ NMR (CDCl$_3$, 300 MHz) δ 1.25–1.31 (m, 9 H), 4.05–4.11 (m, 9 H), 5.48 (d, 1 H, J=8.7 Hz), 6.43 (d, 1H, J=5.1 Hz), 7.03–7.09 (m, 2 H), 7.41–7.46 (m, 2 H), 8.17 (d, 1 H, J=5.1 Hz); HRMS: Calc. for $C_{23}H_{26}FN_5O_4$ 456.2047 (M$^+$+H), Found 456.2059.

Spiro[1,3-dioxolane[2',6]-2-(4-fluorophenyl)-3-[2-(cyclopropylamino)pyrimidin-4-yl]6,7-dihydro-5H-pyrazolo[1,2-a]pyrazol-1-one]: $^1H$ NMR (CDCl$_3$, 300 MHz) δ 0.59–0.64 (m, 2 H), 0.87 (q, 2H, J=12.3, 6 Hz), 2.78–2.82 (m, 1 H), 4.06–14.11 (m, 6 H), 4.23 (s, 2 H), 5.50 (s, 1 H), 6.50 (d, 1 H, J=5.1 Hz), 7.04–7.10 (m, 2 H), 7.42–7.47 (m, 2 H), 8.23 (d, 1 H, J=5.1 Hz). ESI$^-$ MS: m/z (rel. intensity) 410.24 (100, M$^+$+H).

Spiro[1,3-dioxolane[2',6]-2-(4-fluorophenyl)-3-[2-(2-fluoro-benzylamino)pyrimidin-4-yl]-6,7-dihydro-5H-pyrazolo[1,2-a]pyrazol-1-one]: $^1H$ NMR (CDCl$_3$, 300 MHz) δ 3.96–4.10 (m, 8 H), 4.74 (d, 2 H, J=6.3 Hz), 5.73 (s, 1 H), 6.47 (d, 1 H, J=5.1 Hz), 7.03–7.16 (m, 4 H), 7.26–7.45 (m, 4 H), 8.22 (d, 1 H, J=5.1 Hz). ESI$^-$ MS: m/z (rel. intensity) 478.1 (100, M$^+$+H). Anal. Calculated for $C_{25}H_{21}F_2N_5O_3$ 0.75$H_2O$: C, 61.16; H, 4.62; N, 14.26. Found: C, 61.26; H, 4.39; N, 14.13.

Spiro[1,3-dioxolane[2',6]-2-(4-fluorophenyl)-3-[2-(3-fluoro-benzylamino)pyrimidin-6,7-dihydro-5H-pyrazolo[1,2-a]pyrazol-1-one]: $^1H$ NMR (CDCl$_3$, 300 MHz) δ 3.964.05 (m, 8 H), 4.69 (d, 2 H, J=6.3 Hz), 5.79 (s, 1 H), 6.49 (d, 1 H, J=5.1 Hz), 6.98–7.16 (m, 4 H), 7.28–7.45 (m, 4 H), 8.23 (d, 1 H, J=5.1 Hz). ESI$^-$ MS: m/z (rel. intensity) 478.1 (100, M$^+$+H). Anal. Calculated for $C_{25}H_{21\ F2}N_5O_3$ 0.5$H_2O$: C, 61.72; H, 4.56; N, 14.40. Found: C, 61.84; H, 4.21; N, 14.28.

Spiro[1,3-dioxolane[2',6]-2-(4-fluorophenyl)-3-12-(2-trifluoromethyl-benzylamino)pyrimidin-4-yl]-6,7-dihydro-5H-pyrazolo[1,2-a]pyrazol-1-one]: $^1H$ NMR (CDCl$_3$, 300 MHz) δ 3.95–4.08 (m, 8 H), 4.91 (d, 2H, J=6.0 Hz), 5.79 (s, 1 H), 6.50 (d, 1 H, J=5.1 Hz), 7.06 (t, 2 H, J=8.7 Hz), 7.39–7.44 (m, 3 H), 7.52–7.57 (m, 2 H), 7.72 (d, 1 H, J=7.8 Hz), 8.23 (d, 1 H, J=5.1 Hz). ESI$^-$ MS: m/z (rel. intensity) 528.2 (100, M$^+$+H).

Spiro[1,3-dioxolane[2',6]-2-(4-fluorophenyl)-3-[2-(3-trifluoromethyl-benzylamino)pyrimidin-4-yl]4,7-dihydro-5H-pyrazolo[1,2-a]pyrazol-1-one]: $^1H$ NMR (CDCl$_3$, 300 MHz) δ 3.94–4.04 (m, 8 H), 4.75 (d, 2 H, J=6.3 Hz), 5.79 (s, 1 H), 6.50 (d, 1 H, J=5.1 Hz), 7.03–7.08 (m, 2 H), 7.39–7.62 (m, 6 H), 8.24 (d, 1 H, J=5.1 Hz). ESI$^-$ MS: m/z (rel intensity) 528.24 (100, M$^+$+H).

Spiro[1,3-dioxolane[2',6]-2-(4-fluorophenyl)-3-[2-(2-fluoro-benzylamino)pyrimidin-4-yl]6,7-dihydro-5H-pyrazolo[1,2-a]pyrazol-1-one]: $^1H$ NMR (CDCl$_3$, 300 MHz) δ 3.90–4.03 (m, 8 H), 4.75 (d, 2 H, J=6.0 Hz), 5.86 (s, 1 H), 6.49 (d, 1 H, J=5.1 Hz), 7.02–7.08 (m, 2 H), 7.39–7.50 (m, 4 H), 7.63 (d, 2 H, J=8.4 Hz), 8.23 (d, 1 H, J=5.1 Hz). ESI⁻ MS: m/z (rel intensity) 528.24 (40, M⁺+H).

The analogs encompassed by the second aspect of Category I compounds can be prepared by substituting 1,3-propylene glycol for ethylene glycol in the preparation of intermediate 5 as described herein to afford intermediate 11.

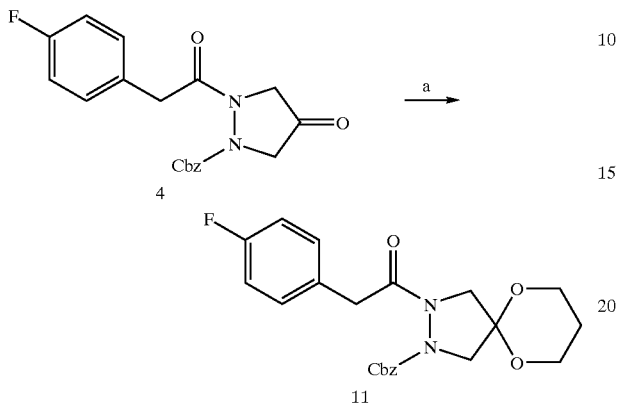

Reagents and Conditions: (a) propylene glycol, TsOH, toluene, reflux 18 hr.

Spiro[5',5'-dimethyl-1,3-dioxane[2',6]-2-(4-fluorophenyl)-3-[2-(1-(S)-methylbenzylamino)-pyrimidin-4-yl]-6,7-dihydro-5H-pyrazolo[1,2-a]pyrazol-1-one]: ¹H NMR (CDCl₃, 300MHz) δ 0.92 (s, 3 H), 1.13 (s, 3 H), 1.61 (d, 3 H, J=6.9 Hz), 3.45–3.58 (m, 5 H), 3.84 (br s, 1 H), 4.07–4.11 (m, 1 H), 4.31 (d, 1 H, J=11.4 Hz), 5.18 (quint, 1 H, J=6.6 Hz), 5.64 (d, 1 H, J=6.9 Hz), 6.41 (d, 1 H, J=4.8 Hz), 7.04 (t, 2 H, J=8.7 Hz), 7.28–7.42 (m, 7 H), 8.18 (d, 1 H, J=4.8 Hz). ESI⁻ MS: m/z (rel intensity) 516.2 (100, M⁺+H) Anal. Calculated for C₂₉H₃₀FN₅O₃: C, 67.56; H, 5.86; N, 13.58. Found: C, 67.46; H, 5.44; N, 13.42.

Spiro[5',5'-dimethyl-1,3-dioxane[2',6]-2-(4-fluorophenyl)-3-[2-(1-(S)-methy-2-methoxy-ethylamino)pyrimidin-4-yl]-6,7-dihydro-5H-pyrazolo[1,2-a]pyrazol-1-one]: ¹H NMR (CDCl₃, 300 MHz) δ 0.95 (s, 3 H), 1.14 (s, 3 H), 1.32 (d, 3 H, J=6.6 Hz), 3.43 (s, 3 H), 3.48 (d, 2 H, J=4.5 Hz), 3.61 (dd, 4H, J=16.5, 11.4 Hz), 4.25 (d, 4 H, J=10.2 Hz), 5.43 (d, 1 H, J=7.5 Hz), 6.42 (d, 1 H, J=5.1 Hz), 7.03–7.09 (m, 2 H), 7.41–7.46 (m, 2 H), 8.19 (d, 1 H, J=5.1 Hz). ESI⁻ MS: m/z (rel. intensity) 484.1 (100, M⁺+H).

The first aspect of Category II inflammatory cytokine release inhibiting compounds according to the present invention are ethers having the general scaffold having the formula:

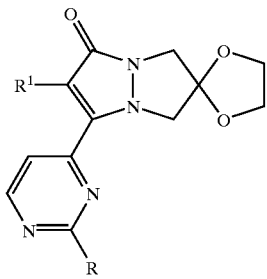

which are 2',6-spiro[1,3-dioxolane] derivatives of 6,7-dihydro-5H-pyrazolo[1,2-a]pyrazol-1-ones wherein R units have the formula —OR³. Table III herein below provides non-limiting examples of R¹, and R³.

TABLE III

| No. | R¹ | R³ |
|---|---|---|
| 41 | 4-fluorophenyl | phenyl |
| 42 | 4-fluorophenyl | 2-fluorophenyl |
| 43 | 4-fluorophenyl | 3-fluorophenyl |
| 44 | 4-fluorophenyl | 4-fluorophenyl |
| 45 | 4-fluorophenyl | 2,6-difluorophenyl |
| 46 | 4-fluorophenyl | 2-cyanophenyl |
| 47 | 4-fluorophenyl | 3-cyanophenyl |
| 48 | 4-fluorophenyl | 2-trifluoromethylphenyl |
| 49 | 4-fluorophenyl | 4-trifluoromethylphenyl |
| 50 | 4-fluorophenyl | 2-methylphenyl |
| 51 | 4-fluorophenyl | 4-methylphenyl |
| 52 | 4-fluorophenyl | 2,4-dimethylphenyl |
| 53 | 4-fluorophenyl | 3-N-acetylaminophenyl |
| 54 | 4-fluorophenyl | 2-methoxyphenyl |
| 55 | 4-fluorophenyl | 4-methoxyphenyl |
| 56 | 4-fluorophenyl | 2-(methanesulfonyl)phenyl |
| 57 | 4-fluorophenyl | 4-(methanesulfonyl)phenyl |
| 58 | 4-fluorophenyl | 2-(propanesulfonyl)phenyl |
| 59 | 4-fluorophenyl | 4-(propanesulfonyl)phenyl |
| 60 | 4-fluorophenyl | 3-benzo[1,3]dioxol-5-yl |

The second aspect of Category II inflammatory cytokine release inhibiting compounds according to the present invention comprise the general scaffold having the formula:

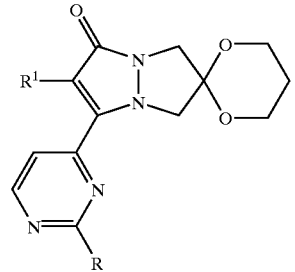

which are 2',6-spiro[1,3-dioxane] derivatives of 6,7-dihydro-5H-pyrazolo[1,2-a]pyrazol-1-ones wherein R units have the formula —OR³. Table IV herein below provides non-limiting examples of R¹, and R³.

TABLE IV

| No. | R¹ | R³ |
|---|---|---|
| 61 | 4-fluorophenyl | phenyl |
| 62 | 4-fluorophenyl | 2-fluorophenyl |
| 63 | 4-fluorophenyl | 3-fluorophenyl |
| 64 | 4-fluorophenyl | 4-fluorophenyl |
| 65 | 4-fluorophenyl | 2,6-difluorophenyl |
| 66 | 4-fluorophenyl | 2-cyanophenyl |
| 67 | 4-fluorophenyl | 3-cyanophenyl |
| 68 | 4-fluorophenyl | 2-trifluoromethylphenyl |
| 69 | 4-fluorophenyl | 4-trifluoromethylphenyl |
| 70 | 4-fluorophenyl | 2-methylphenyl |
| 71 | 4-fluorophenyl | 4-methylphenyl |
| 72 | 4-fluorophenyl | 2,4-dimethylphenyl |
| 73 | 4-fluorophenyl | 3-N-acetylaminophenyl |
| 74 | 4-fluorophenyl | 2-methoxyphenyl |
| 75 | 4-fluorophenyl | 4-methoxyphenyl |
| 76 | 4-fluorophenyl | 2-(methanesulfonyl)phenyl |
| 77 | 4-fluorophenyl | 4-(methanesulfonyl)phenyl |
| 78 | 4-fluorophenyl | 2-(propanesulfonyl)phenyl |
| 79 | 4-fluorophenyl | 4-(propanesulfonyl)phenyl |
| 80 | 4-fluorophenyl | 3-benzo[1,3]dioxol-5-yl |

The compounds which comprise Category II analogs of the present invention are prepared by way of a convergent synthesis wherein the R unit is in place on the pyrimidine ring prior to formation of the final 6,7-dihydro-5H-pyrazolo[1,2-a]pyrazol-1-one scaffold. The following scheme outlines the synthesis of compound 16, and an example of an intermediate in the preparation of Category II compounds.

General Scheme for Preparation of Pyrimidine Ether Intermediates

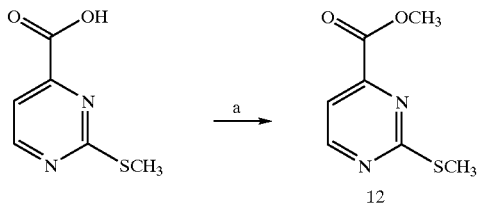

Reagents and conditions: (a) SOCl$_2$, MeOH; rt 12 hr.

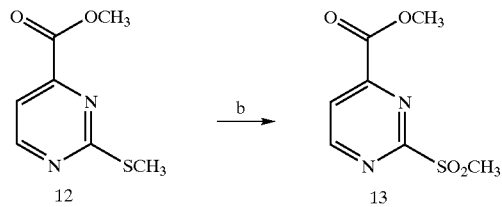

Reagents and conditions: (b) Oxone®, MeOH/THF/H$_2$O; rt 12 hr.

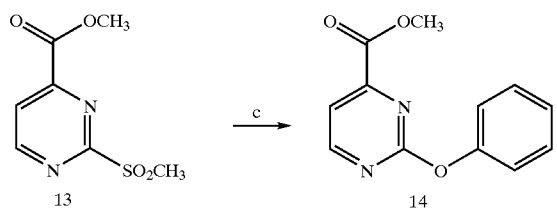

Reagents and conditions: (c) phenol, NaH, THF; rt 12 hr.

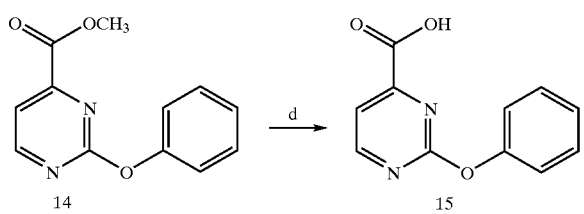

Reagents and conditions: (d) NaOH MeOH/H$_2$O; rt 1.5 hr.

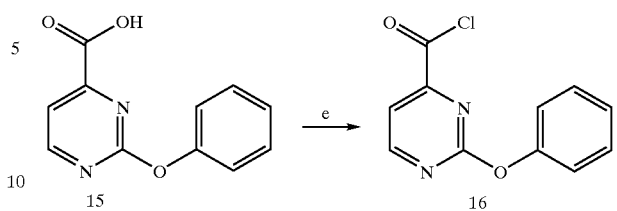

Reagents and conditions: (e) oxalyl chloride, CH$_2$CL$_2$/DMF; rt 2 hr.

EXAMPLE 2

2-Phenoxy-pyrimidine-4-carbonyl chloride (16)

Preparation of 2-methylsulfanyl-pyrimidine-4-carboxylic acid methyl ester (12): To a suspension of 2-methylsulfanyl-pyrimidine-4-carboxylic acid (15 g, 88 mmol) in methanol (200 mL) is added dropwise thionyl chloride (25 mL). The solution is allowed to warm to room temperature and stir 12 hours. The solution is then concentrated in vacuo and the yellow solid which remains can be taken up in methylene chloride and re-concentrated to afford 19 g (97% yield) of the HCl salt of the desired product as a white solid.

Preparation of 2-methanesulfonyl-pyrimidine-4-carboxylic acid methyl ester (13): An aqueous solution (1 L) of Oxone® (211.7 g, 344 mmol) is added dropwise at 0° C. to a solution of 2-methyl-sulfanyl-pyrimidine-4-carboxylic acid methyl ester, 12, (19 g,86.1 mmol) in 1:1 methanol/THF (1 L). The reaction solution is allowed to warm to room temperature and stir for 1.5 hours. The resulting suspension is partitioned between methylene chloride and water. The aqueous phase is made alkaline with the addition of NaOH and re extracted with solvent. The combined organic layers are dried, filtered, and concentrated in vacuo to afford 18.4 g of the desired product as a yellow oil.

Preparation of 2-phenoxy-pyrimidine-4-carboxylic acid methyl ester (14): NaH (3.5 g of a 60% suspension, 87.4 mmol) is added to a solution of phenol (8.23 g, 87.4 mmol) in THF (100 mL) at room temperature. 2-Methanesulfonyl-pyrimidine-4-carboxylic acid methyl ester, 13, (6.3 g, 29.1 mmol) is dissolved in THF (60 mL) and added dropwise to the solution of phenol. The reaction is allowed to stir for 12 hours then quenched by the addition of saturated aqueous NH$_4$Cl. The aqueous phase is extracted with methylene chloride and the combined organic layers are dried, filtered, and concentrated in vacuo to afford a crude oil which is purified over silica (ethyl acetate/hexane 2:3) to afford 1.72 g (25% yield) of the desired product as a white solid.

Preparation of 2-phenoxy-pyrimidine-4-carboxylic acid (15): To a solution of 2-phenoxy-pyrimidine-4-carboxylic acid methyl ester, 14, (1.72 g, 74.8 mmol) in methanol (50 mL) is added a 50% NaOH solution (10 mL) at room temperature. After stirring for 1.5 hours the solvent is removed in vacuo and the remaining aqueous phase is extracted with ethyl acetate. The aqueous phase can then be carefully acidified with concentrated HCl and the white solid which forms extracted twice with ethyl acetate. The organic layers are combined, dried and concentrated in vacuo to afford 0.95 g (60% yield) of the desired product as a white solid.

27

Preparation of 2-phenoxy-pyrimidine-4-carbonyl chloride (16): To a solution of 2-phenoxy-pyrimidine-4-carboxylic acid, 15, (0.19 g, 0.89 mmol) in methylene chloride (10 Ml) containing a few drops of DMF is added oxalyl chloride (0.1 Ml). The solution is stirred for 2 hours at room temperature and concentrated in vacuo to afford the desired product which is used without further purification.

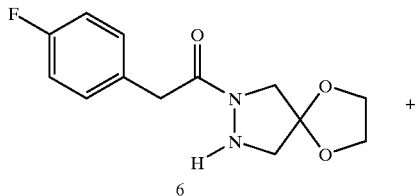

6

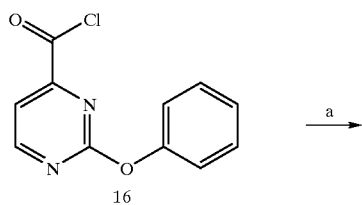

16 a →

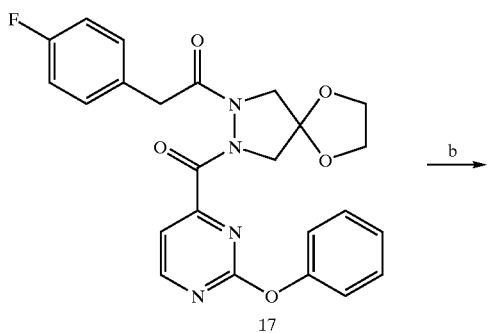

17

Reagents and Conditions: (a) NaOH: CH$_2$Cl$_2$/water, rt 12 hr.

b →

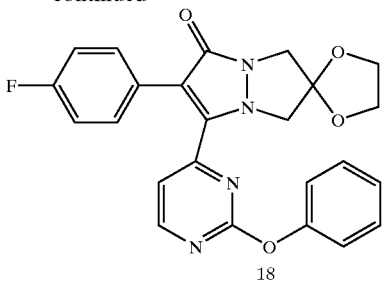

18

Reagents and Conditions: (b) NaH, DMF; 0° C., 2 hr.

EXAMPLE 3

Spiro[1,3-dioxolane[2',6]-2-(4-fluorophenl)-3-(2-phenoxy-pyrimidin-4-yl)-6,7-dihydro-5H-pyrazolo[1,2-a]pyrazol-1-one (18)

Preparation of spiro[1,3-dioxolane[2',6]-2-(4-fluorophenyl)-1-[2-(2-phenoxy-pyrimidine-4carbonyl)pyrazolidine-1-yl]ethanone (17): 2-phenoxy-pyrimidine-4-carbonyl chloride, 16, (0.066 g, 0.28 mmol) in methylene chloride (1.5 mL) is added dropwise to a suspension of Spiro[1,3-dioxolane[2',6]-2-(4-fluorophenyl)-1-pyrazolidin-1-yl-ethanone, 6, (0.05 g, 0.18 mmol) in a 2:5 water/CH$_2$Cl$_2$ solution (7 mL) containing NaOH ( 0.0112 g, 0.28 mmol) at room temperature. The solution is stirred 18 hours and diluted with additional 2:5 water/CH$_2$Cl$_2$. The layers are allowed to separate and the aqueous phase extracted with additional methylene chloride. The organic layers are combined, dried, filtered and concentrated in vacuo to afford the desired product.

Preparation of Spiro[1,3-dioxolane[2',6-]2-(4-fluorophenyl)-3-(2-phenoxy-pyrimidin-4-yl)-6,7-dihydro-5H-pyrazolo[1,2-a]pyrazol-1-one (18): To a solution of spiro[1,3-dioxolane-[2',6]-2-(4-fluorophenyl)-1-[2-(2-phenoxy-pyrimidine-4-carbonyl)pyrazolidine-1-yl]ethanone, 17, (0.19 g, 0.4 mmol) in DMF (10 mL) at 0° C. is added NaH (0.024 g, 0.6 mmol) and the resulting solution is stirred 2 hours. The solvent is removed in vacuo the residue dissolved in methylene chloride and extracted with water, dried, and re-concentrated to afford the desired product.

Spiro[1,3-dioxolane[2',6]-2-(4-fluorophenyl)-3-[(2-fluoro-phenoxy)pyrimidin-4-yl-]-6,7-dihydro-5H-pyrazolo[1,2-a]pyrazol-1-one]: $^1$H NMR (CDCl$_3$, 300 MHz) δ 3.87 (s, 2 H), 3.98–4.12 (m, 6 H), 6.96 (d, 1 H, J=5.4 Hz), 7.09–7.15 (m, 2 H), 7.25–7.43 (m, 6 H), 8.50 (d, 1 H, J=5.4 Hz). ESI$^-$ MS: m/z (rel intensity) 465.2 (100, M$^+$+H). Anal. Calculated for C$_{24}$H$_{18}$F$_2$N$_4$O$_4$ 0.5H$_2$O: C, 60.89; H, 4.05; N, 11.83. Found: C, 61.26; H, 3.72; N, 11.63.

Compounds which comprise the second aspect of Category II can be prepared by substituting intermediate 11 for intermediate 6 in the convergent synthesis outlined herein above.

Spiro[1,3-dioxane[2',6]-2-(4-fluorophenyl)-3-(2-phenoxy-pyrimidin-4-yl)-6,7-dihydro-5H-pyrazolo[1,2-a]pyrazol-1-one]: $^1$H NMR (CDCl$_3$, 300 MHz) δ 1.75–1.94 (m, 2 H), 3.82–3.98 (m, 6 H), 4.24 (s, 2 H), 6.91 (d, 1 H, J=5.4 Hz), 7.08–7.14 (m, 2 H), 7.24–7.42 (m, 5 H), 7.48–7.54 (m, 2 H), 8.49 (d, 1 H, J=5.4 Hz). ESI$^-$ MS: m/z (rel intensity) 460.9 (100, M$^+$+H). Anal. Calculated for $C_{25}H_{21}FN_4O_4 \cdot H_2O$: C, 62.76; H, 4.85; N, 11.71. Found: C, 62.57; H, 4.22; N, 11.57.

The first aspect of Category III inflammatory cytokine release inhibiting compounds according to the present invention are ethers having the general scaffold having the formula:

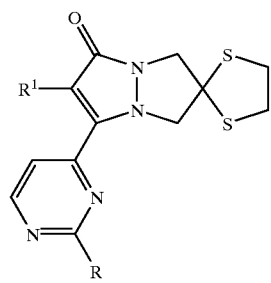

which are 2',6-spiro[1,3-dithioxolane] derivatives of 6,7-dihydro-5H-pyrazolo[1,2-a]pyrazol-1-ones wherein R units have the formula —$OR^3$. Table V herein below provides non-limiting examples of R and $R^1$.

TABLE V

| No. | R | $R^1$ |
|---|---|---|
| 81 | phenoxy | 4-fluorophenyl |
| 82 | 2-fluorophenoxy | 4-fluorophenyl |
| 83 | 3-fluorophenoxy | 4-fluorophenyl |
| 84 | 4-fluorophenoxy | 4-fluorophenyl |
| 85 | 2,6-difluorophenoxy | 4-fluorophenyl |
| 86 | 2-cyanophenoxy | 4-fluorophenyl |
| 87 | 3-cyanophenoxy | 4-fluorophenyl |
| 88 | 2-trifluoromethylphenoxy | 4-fluorophenyl |
| 89 | 4-trifluoromethylphenoxy | 4-fluorophenyl |
| 90 | 2-methylphenoxy | 4-fluorophenyl |
| 91 | 4-methylphenoxy | 4-fluorophenyl |
| 92 | 2,4-dimethylphenoxy | 4-fluorophenyl |
| 93 | 3-N-acetylaminophenoxy | 4-fluorophenyl |
| 94 | 2-methoxyphenoxy | 4-fluorophenyl |
| 95 | 4-methoxyphenoxy | 4-fluorophenyl |
| 96 | 3-benzo[1,3]dioxol-5-yl | 4-fluorophenyl |
| 97 | phenoxy | 3-(trifluoromethyl)phenyl |
| 98 | 2-fluorophenoxy | 3-(trifluoromethyl)phenyl |
| 99 | 3-fluorophenoxy | 3-(trifluoromethyl)phenyl |
| 100 | 4-fluorophenoxy | 3-(trifluoromethyl)phenyl |
| 101 | 2,6-difluorophenoxy | 3-(trifluoromethyl)phenyl |
| 102 | 2-cyanophenoxy | 3-(trifluoromethyl)phenyl |
| 103 | 3-cyanophenoxy | 3-(trifluoromethyl)phenyl |
| 104 | 2-trifluoromethylphenoxy | 3-(trifluoromethyl)phenyl |
| 105 | 4-trifluoromethylphenoxy | 3-(trifluoromethyl)phenyl |
| 106 | 2-methylphenoxy | 3-(trifluoromethyl)phenyl |
| 107 | 4-methylphenoxy | 3-(trifluoromethyl)phenyl |
| 108 | 2,4-dimethylphenoxy | 3-(trifluoromethyl)phenyl |
| 109 | 3-N-acetylaminophenoxy | 3-(trifluoromethyl)phenyl |
| 110 | 2-methoxyphenoxy | 3-(trifluoromethyl)phenyl |
| 111 | 4-methoxyphenoxy | 3-(trifluoromethyl)phenyl |
| 112 | 3-benzo[1,3]dioxol-5-yl | 3-(trifluoromethyl)phenyl |
| 113 | phenoxy | 4-chlorophenyl |
| 114 | 2-fluorophenoxy | 4-chlorophenyl |
| 115 | 3-fluorophenoxy | 4-chlorophenyl |
| 116 | 4-fluorophenoxy | 4-chlorophenyl |
| 117 | 2,6-difluorophenoxy | 4-chlorophenyl |
| 118 | 2-cyanophenoxy | 4-chlorophenyl |
| 119 | 3-cyanophenoxy | 4-chlorophenyl |
| 120 | 2-trifluoromethylphenoxy | 4-chlorophenyl |
| 121 | 4-trifluoromethylphenoxy | 4-chlorophenyl |
| 122 | 2-methylphenoxy | 4-chlorophenyl |
| 123 | 4-methylphenoxy | 4-chlorophenyl |
| 124 | 2,4-dimethylphenoxy | 4-chlorophenyl |
| 125 | 3-N-acetylaminophenoxy | 4-chlorophenyl |
| 126 | 2-methoxyphenoxy | 4-chlorophenyl |
| 127 | 4-methoxyphenoxy | 4-chlorophenyl |
| 128 | 3-benzo[1,3]dioxol-5-yl | 4-chlorophenyl |

The following scheme provides methods for preparing the compounds of Category II according to the present invention.

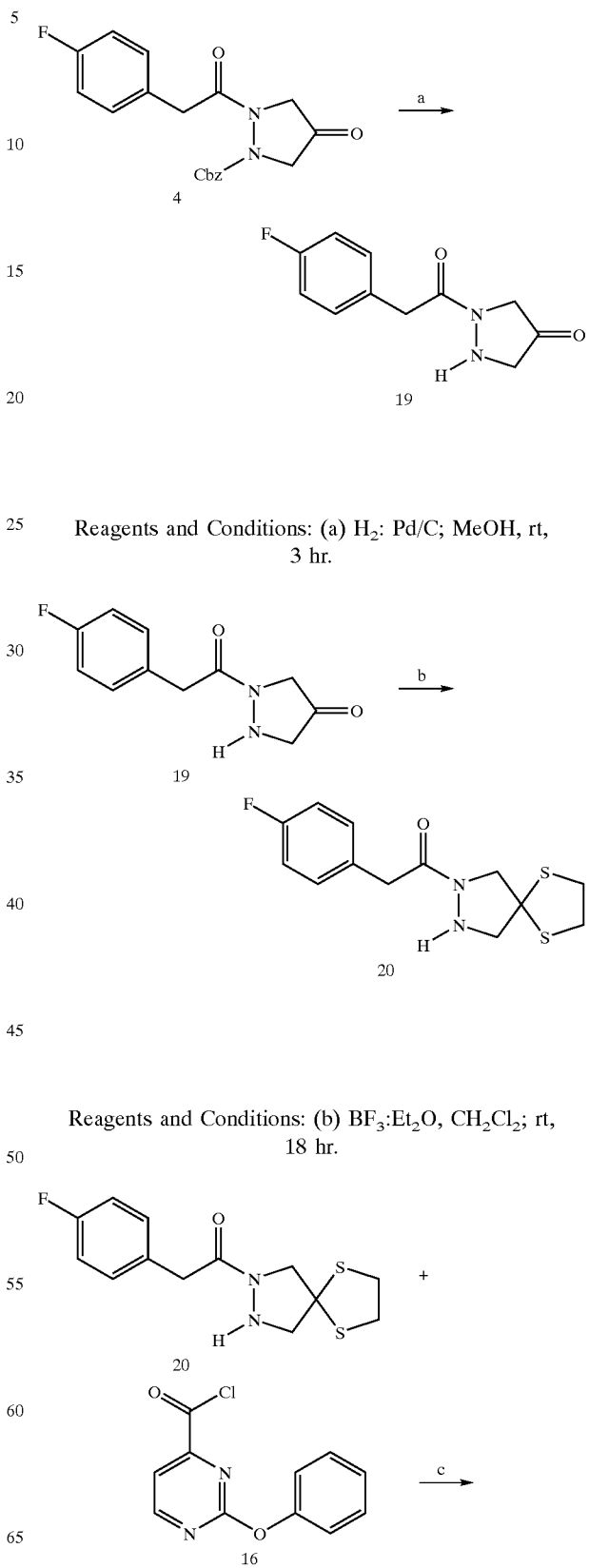

Reagents and Conditions: (a) $H_2$: Pd/C; MeOH, rt, 3 hr.

Reagents and Conditions: (b) $BF_3:Et_2O$, $CH_2Cl_2$; rt, 18 hr.

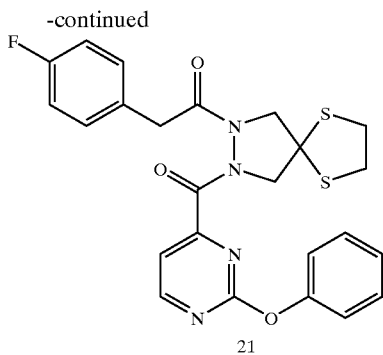

Reagents and Conditions: (c) NaOH, CH$_2$Cl$_2$/water, rt, 18 hr.

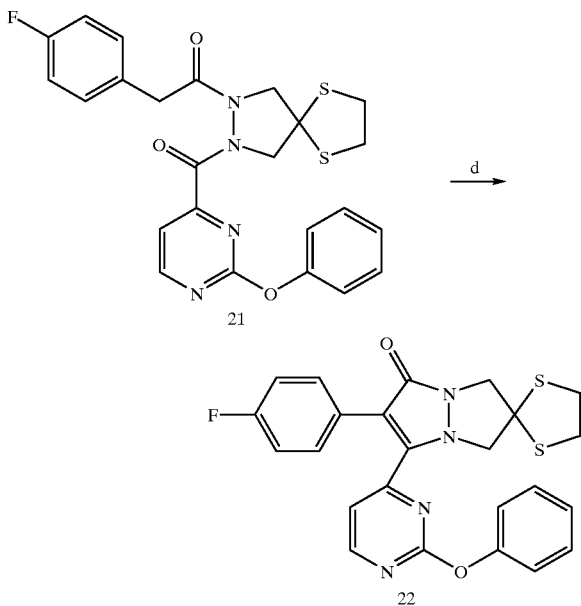

Reagents and Conditions: (d) NaH, DMF, −5° C., 1 hr.

EXAMPLE 4

Spiro[1,3-dithiolane[2',6]-2-(4-fluorophenyl)-3-(2-phenoxy-pyrimidin-4-yl)-6,7-dihydro-5H-pyrazolo[1,2-a]pyrazol-1-one] (22)

Preparation of 1-[2-(4-fluorophenyl)acetyl]-pyrazolidin-4-one (19): To a solution of 2-[2-(4-fluorophenyl)acetyl]-4-oxo-pyrazolidine-1-carboxylic acid benzyl ester, 4, (1 g, 4.5 mmol) in methanol (30 mL) is added Pd/C (100 mg). A balloon filled with hydrogen gas is placed over the flask and the mixture stirred for 3 hours. The solution is filtered to remove the catalyst and concentrated in vacuo to afford 0.8 g of the desired product as a yellow oil which is used without further purification.

Preparation of spiro[1,3-dithiolane[2',4]-2-[(4-fluorophenyl)-1-pyrazolidin-1-yl]ethanone] (20): To a solution of 1-[2-(4-fluorophenyl)acetyl]-pyrazolidin4-one, 19, (0.4 g, 1.8 mmol), and 1,2-ethanedithiol (0.23 mL, 2.7 mmol) in methylene chloride (13 mL) is added boron trifluoride etherate (0.4 mL). The reaction is allowed to stir 18 hours after which the solution is extracted with 0.1 N HCl, brine, dried, and concentrated in vacuo to afford the crude product which is used without further purification.

Preparation of spiro[1,3-dithiolane[2',4]-2-(4-fluorophenyl)-1-[2-(2-phenoxypyrimidine-4-carbonyl)pyrazolidine-1-yl]-ethanone] (21): To a suspension of spiro[1,3-dithiolane[2',4]-2-[(4-fluorophenyl)-1-pyrazolidin-1-yl]-ethanone], 20, (0.25 g, 0.83 mmol) and NaOH (0.05 g, 1.2 mmol) in 5:3 methylene chloride/water (8 mL) is added 2-phenoxy-pyrimidine-4-carbonyl chloride, 16, (0.295 g, 1.2 mmol). The reaction solution is stirred at room temperature for 18 hours after which time the layers are separated and the organic phase washed with 20% NaHCO$_3$, brine, dried, and concentrated in vacuo to afford a crude residue which is purified by prep HPLC to afford 0.35 g of the desired product.

Preparation of spiro[1,3-dithiolane[2',6]-2-(4-fluorophenyl)-3-(2-phenoxy-pyrimidin-4-yl)6,7-dihydro-5H-pyrazolo[1,2-a]pyrazol-1-one] (22): NaH (0.42 9, 1.1 mmol) is added to a solution of spiro[1,3-dithiolane[2',4]-2-(4-fluorophenyl)-1-[2-(2-phenoxypyrimidine-4-carbonyl)pyrazolidine-1-yl]-ethanone], 21, (0.35 g, 0.7 mmol) in DMF (5 mL) at −5° C. and the reaction is stirred for 1 hour in the cold. The reaction solution is diluted with methylene chloride and washed with 0.1 N HCl. The acid layer is made alkaline and extracted with methylene chloride, the organic layers combined, washed with brine, dried and concentrated in vacuo to afford 0.1 9 (30% yield) of the desired product. $^1$H NMR (CDCl$_3$, 300 MHz) δ 3.35–3.50 (m, 4 H), 4.09 (s, 2 H), 4.46 (s, 2 H), 6.93 (d, 1 H, J=5.1 Hz), 7.10–7.17 (m, 2 H), 7.23–7.43 (m, 5 H), 7.48–7.53 (m, 2 H), 8.52 (d, 1 H, J=5.1 Hz). ESI$^-$ MS: m/z (rel intensity) 478.9 (100, M$^+$+H) Anal. Calculated for C$_{24}$H$_{19}$FN$_4$O$_2$S$_2$ 0.5 H$_2$O: C, 59.12; H, 4.13; N, 11.49. Found: C, 58.87; H, 3.95; N, 11.91.

The following are non-limiting example of other compounds according to the present invention.

Spiro[1,3-dioxane[2',6]-2-(4-fluorophenyl)-3-[(2-(S)-(α)-methyl-benzylamino)pyrimidin-4-yl]-6,7-dihydro-5H-pyrazolo[1,2-a]pyrazol-1-one];

Spiro[1,3-dioxane[2',6]-2-(4-fluorophenyl)-3-[2-(1,1-dimethylethylamino)pyrimidin-4-yl]-6,7-dihydro-5H-pyrazolo[1,2-a]pyrazol-1-one];

Spiro[1,3-dioxane[2',6]-2-(4-fluorophenyl)-3-[2-(benzylamino)pyrimidin-4-yl]-6,7-dihydro-5H-pyrazolo[1,2-a]pyrazol-1-one];

Spiro[1,3-dioxane[2',6-]2-(4-fluorophenyl)-3-{2-[(2-methylphenyl)methylamino]pyrimidin-4-yl}-6,7-dihydro-5H-pyrazolo[1,2-a]pyrazol-1-one].

The analogs (compounds) of the present invention are arranged in several categories to assist the formulator in applying a rational synthetic strategy for the preparation of analogs which are not expressly exampled herein. The arrangement into categories does not imply increased or decreased efficacy for any of the compositions of matter described herein.

Compounds listed and described herein above have been found in many instances to exhibit activities (IC$_{50}$ in the cell based assay described herein below or ones which are referenced herein) at a level below 1 micromolar ($\mu$M).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines. Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease states which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBS), septic shock, cardiopulmonary dysfunction, acute respiratory disease, and cachexia.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor of "pro-drug" forms of the analogs of the present invention. It may be desirable to formulate the compounds of the present invention as a chemical species which itself is not active against the cytokine activity described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

Formulations

The present invention also relates to compositions or formulations which comprise the inflammatory cytokine release-inhibiting compounds according to the present invention. In general, the compositions of the present invention comprise:

a) an effective amount of one or more bicyclic pyrazolones and derivatives thereof according to the present invention which are effective for inhibiting release of inflammatory cytokines; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the inflammatory cytokine release-inhibiting compounds according to the present invention. In general, these precursor-comprising compositions of the present invention comprise:

a) an effective amount of one or more derivatives of bicyclic pyrazolones according to the present invention which act to release in vivo the corresponding analog which is effective for inhibiting release of inflammatory cytokines; and b) one or more pharmaceutically acceptable excipients.

Method Of Use

The present invention also relates to a method for controlling the level of one or more inflammation inducing cytokines, inter alia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

Procedures

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:

i) UV-visible substrate enzyme assay as described by L. Al Reiter, *Int. J. Peptide Protein Res.*, 43, 87–96 (1994).

ii) Fluorescent substrate enzyme assay as described by Thornberry et al., *Nature*, 356, 768–774 (1992).

iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:

i) K. M. Mohler et al., "Protection Against a Lethal Dose of Endotoxin by an Inhibitor of Tumour Necrosis Factor Processing", *Nature*, 370, pp 218–220 (1994).

ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNFα in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells ($2 \times 10^6$ cells/mL, final conc.; American Type Culture Company, Rockville, Md.) are added to 96 well polypropylene round bottomed culture plates (Costar 3790; sterile) containing 125 μL test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 μg/mL final; Sigma L-2630, from *E. coli* serotype 0111.B4; stored as 1 mg/mL stock in endotoxin screened diluted $H_2O$ vehicle at −80° C.). Blanks (unstimulated) receive $H_2O$ vehicle; final incubation volume is 250 μL. Incubation (4 hours) proceeds as described above. Assay is to be terminated by centrifuging plates 5 minutes at room temperature, 1600 rpm (4033 g); supernatants are then transferred to clean 96 well plates and stored at −80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, or all enantiomeric and diasteriomeric forms or pharmaceutically acceptable salts thereof, said compound having the formula:

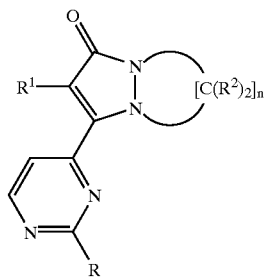

wherein R is:
a) —O[CH$_2$]$_k$R$^3$; or
b) —NR$^{4a}$R$^{4b}$;
R$^3$ is substituted or unsubstituted C$_1$–C$_4$ alkyl, substituted or unsubstituted hydrocarbyl, substituted or unsubstituted heterocyclyl, substituted or unsubstituted aryl or alkylenearyl, substituted or unsubstituted heteroaryl or alkyleneheteroaryl; the index k is from 0 to 5;

R$^{4a}$ and R$^{4b}$ are each independently:
a) hydrogen; or
b) —[C(R$^{5a}$R$^{5b}$)]$_m$R$^6$;
each R$^{5a}$ and R$^{5b}$ are independently hydrogen, or C$_1$–C$_4$ linear, branched, or cyclic alkyl, and mixtures thereof; R$^6$ is —OR$^7$, —N(R$^7$)$_2$, —CO$_2$R$^7$, —CON(R$^7$)$_2$; substituted or unsubstituted C$_1$–C$_4$ alkyl, substituted or unsubstituted aryl, or substituted or unsubstituted heteroaryl; R$^7$ is hydrogen, a water-soluble cation, or C$_1$–C$_4$ alkyl; the index m is from 0 to 5;

R$^1$ is:
a) substituted or unsubstituted aryl; or
b) substituted or unsubstituted heteroaryl;
two R$^2$ units on the same carbon atom are taken together to form a spirocyclic ring having from 4 to 7 atoms, the balance of the R$^2$ units are independently selected from the group consisting of:
a) hydrogen;
b) —O(CH$_2$)$_j$R$^8$;
c) —(CH$_2$)$_j$NR$^{9a}$R$^{9b}$;
d) —(CH$_2$)$_j$CO$_2$R$^{10}$;
e) —(CH$_2$)$_j$OCO$_2$R$^{10}$
f) —(CH$_2$)$_j$CON(R$^{10}$)$_2$; and
g) two R$^2$ units can be taken together to form a carbonyl unit;
R$^8$, R$^{9a}$, R$^{9b}$, and R$^{10}$ are each independently hydrogen, C$_1$–C$_4$ alkyl; or R$^{9a}$ and R$^{9b}$ can be taken together to form a carbocyclic or heterocyclic ring having from 3 to 7 atoms; two R$^{10}$ units can be take together to form a carbocyclic or heterocyclic ring having from 3 to 7 atoms; j is an index from 0 to 5; the index n is from 3 to 5.

2. A compound according to claim 1 having the formula:

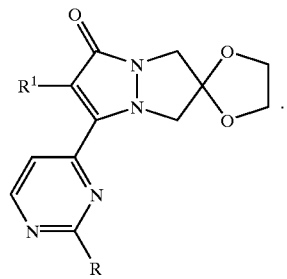

3. A compound according to claim 2 wherein R$^1$ is 4-fluorophenyl.

4. A compound according to claim 2 wherein R is a unit having the formula —OR$^3$ wherein R$^3$ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetylaminophenyl, 2-methoxyphenyl, 4-methoxyphenyl, and 3-benzo[1,3] dioxol-5-yl.

5. A compound according to claim 2 wherein R is a unit having the formula:

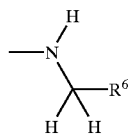

wherein R⁶ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl.

6. A compound according to claim 2 wherein R is a unit having the formula:

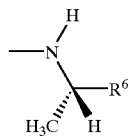

wherein R⁶ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl.

7. A compound according to claim 1 having the formula:

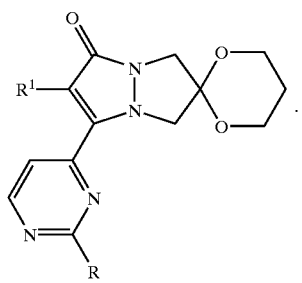

8. A compound according to claim 7 wherein R¹ is 4-fluorophenyl.

9. A compound according to claim 7 wherein R is a unit having the formula —OR³ wherein R³ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetylaminophenyl, 2-methoxyphenyl, 4-methoxyphenyl, and 3-benzo[1,3]dioxol-5-yl.

10. A compound according to claim 7 wherein R is a unit having the formula:

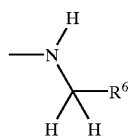

wherein R⁶ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl.

11. A compound according to claim 7 wherein R is a unit having the formula:

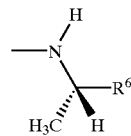

wherein R⁶ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl.

12. A compound according to claim 7 wherein R is a unit having the formula:

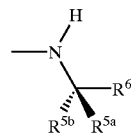

$R^{5a}$ and $R^{5b}$ are each $C_1$–$C_4$ alkyl, R⁶ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxy-phenyl, 4-(propanesulfonyl)phenyl, 3-benzo[1,3]dioxol-5-yl, pyridin-2-yl, pyridin-3-yl, said R unit has the indicated stereochemistry when $R^{5a}$, $R^{5b}$ and R⁶ are not the same.

13. A compound according to claim 1 having the formula:

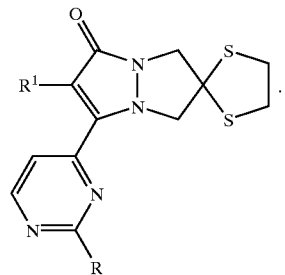

14. A compound according to claim 13 wherein R¹ is 4-fluorophenyl.

15. A compound according to claim 14 wherein R is a unit having the formula —OR³ wherein R³ is selected from the group consisting of phenyl, 2-fluorophenyl, 3-fluorophenyl, 4-fluoro-phenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetylaminophenyl, 2-methoxyphenyl, 4-methoxyphenyl, and 3-benzo[1,3]dioxol-5-yl.

16. A compound according to claim 14 wherein R is a unit having the formula:

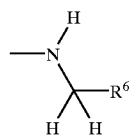

wherein $R^6$ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl.

17. A compound according to claim 14 wherein R is a unit having the formula:

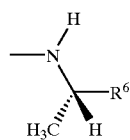

wherein $R^6$ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl.

18. A compound according to claim 1 having the formula:

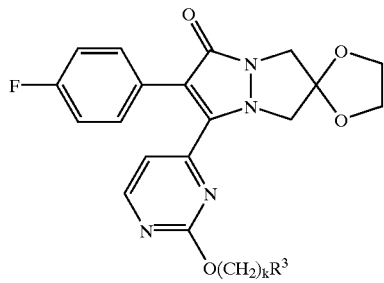

wherein $R^3$ is substituted or unsubstituted $C_1$–$C_4$ alkyl, substituted or unsubstituted hydrocarbyl, substituted or unsubstituted heterocyclyl, substituted or unsubstituted aryl or alkylenearyl, substituted or unsubstituted heteroaryl or alkyleneheteroaryl; the index k is from 0 to 5.

19. A compound according to claim 17 wherein $R^3$ is selected from the group consisting of phenyl, 2-fluorophenyl, 3-fluorophenyl, 4-fluoro-phenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetyl-aminophenyl, 2-methoxyphenyl, 4-methoxyphenyl, and 3-benzo[1,3]dioxol-5-yl.

20. A compound according to claim 1 having the formula:

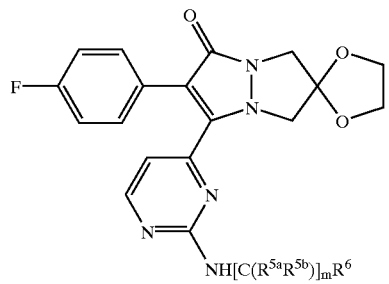

wherein each $R^{5a}$ and $R^{5b}$ are independently hydrogen, —$OR^7$, —$N(R^7)_2$, —$CO_2R^7$, —$CON(R^7)_2$; $C_1$–$C_4$ linear, branched, or cyclic alkyl, and mixtures thereof; $R^6$ is hydrogen, —$OR^7$, —$N(R^7)_2$, —$CO_2R^7$, —$CON(R^7)_2$; substituted or unsubstituted $C_1$–$C_4$ alkyl, substituted or unsubstituted aryl heterocyclic, substituted or unsubstituted aryl, or substituted or unsubstituted heteroaryl; $R^7$ is hydrogen, a water-soluble cation $C_1$–$C_4$ alkyl, or substituted or unsubstituted aryl; the index m is 0 to 5.

21. A compound according to claim 19 wherein $R^6$ is selected from the group consisting of hydrogen, methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxy-phenyl, 4-(propanesulfonyl)phenyl, 3-benzo[1,3]dioxol-5-yl, pyridin-2-yl, pyridin-3-yl.

22. A compound according to claim 21 wherein $R^{5a}$ and $R^{5b}$ are each independently hydrogen or $C_1$–$C_4$ alkyl.

23. A compound according to claim 21 wherein $R^{5a}$ is hydrogen and $R^{5b}$ is methyl.

24. A compound according to claim 1 having the formula:

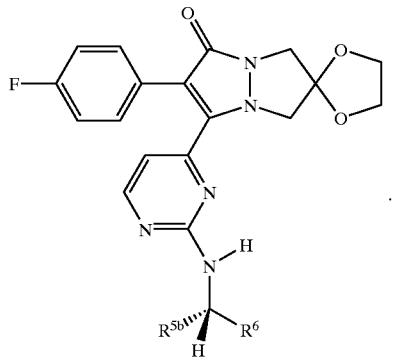

25. A compound according to claim 24 wherein $R^{5b}$ is methyl; $R^6$ is selected from the group consisting of —OH, —$NH_2$, —$CO_2H$, —$CO_2CH_3$, and —$CONH_2$.

26. A compound according to claim 24 wherein $R^{5b}$ is methyl; $R^6$ is selected from the group consisting of methyl, ethyl, vinyl, cyclopropyl, cyclohexyl, methoxymethyl, methoxyethyl, 1-hydroxy-1-methylethyl, carboxy, phenyl, 4-fluorophenyl, 2-aminophenyl, 2-methylphenyl, 4-methylphenyl, 4-methoxy-phenyl, 4-(propanesulfonyl)phenyl, 3-benzo[1,3]dioxol-5-yl, pyridin-2-yl, and pyridin-3-yl.

27. A compound according to claim 1 selected from the group consisting of:

Spiro[1,3-dioxolane[2',6]-2-(4-fluorophenyl)-3-[(2-(S)-(α)-methyl-benzylamino)pyrimid-4-yl]-6,7-dihydro-5H-pyrazolo[1,2-a]pyrazol-1-one];

Spiro[1,3-dioxolane[2',6]-2-(4-fluorophenyl)-3-[2-(1-(S)-methyl-2-methoxyethylamino)-pyrimidin-4-yl]-6,7-dihydro-5H-pyrazolo[1,2-a]pyrazol-1-one];

Spiro[1,3-dioxolane[2',6]-2-(4-fluorophenyl)-3-[2-(benzylamino)pyrimidin-4-yl]-6,7-dihydro-5H-pyrazolo[1,2-a]pyrazol-1-one];

Spiro[1,3-dioxolane[2',6]-2-(4-fluorophenyl)-3-[2-( 1-(S)-methyl-2-hydroxy-2-methylpropylamino)pyrimidin-4-yl]-6,7-dihydro-5H-pyrazolo[1,2-a]pyrazol-1-one];

Spiro[1,3-dioxolane[2',6]-2-(4-fluorophenyl)-3-[2-(cyclopropylamino)pyrimidin-4-yl]-6,7-dihydro-5H-pyrazolo[1,2-a]pyrazol-1-one];

Spiro[1,3-dioxolane[2',6]-2-(4-fluorophenyl)-3-[2-(2-fluoro-benzylamino)pyrimidin-4-yl]6,7-dihydro-5H-pyrazolo[1,2-a]pyrazol-1-one];

Spiro[1,3-dioxolane[2',6]-2-(4-fluorophenyl)-3-[2-(3-fluoro-benzylamino)pyrimidin-4-yl]-6,7-dihydro-5H-pyrazolo[1,2-a]pyrazol-1-one];

Spiro[1,3-dioxolane[2',6]-2-(4-fluorophenyl)-3-[2-(2-trifluoromethyl-benzylamino)pyrimidin-4-yl]-6,7-dihydro-5H-pyrazolo[1,2-a]pyrazol-1-one];

Spiro[1,3-dioxolane[2',6]-2-(4-fluorophenyl)-3-[2-(3-trifluoromethyl-benzylamino)pyrimidin-4-yl]-6,7-dihydro-5H-pyrazolo[1,2-a]pyrazol-1-one];

Spiro[1,3-dioxolane[2',6]-2-(4-fluorophenyl)-3-[2-(2-fluoro-benzylamino)pyrimidin-4-yl]-6,7-dihydro-5H-pyrazolo[1,2-a]pyrazol-1-one];

Spiro[5',5'-dimethyl-1,3-dioxane[2',6]-2-(4-fluorophenyl)-3-[2-(1-(S)-methylbenzlamino)-pyrimidin-4-yl]-6,7-dihydro-5H-pyrazolo[1,2-a]pyrazol-1-one];

Spiro[5',5'-dimethyl-1,3-dioxane[2',6]-2-(4-fluorophenyl)-3-[2-(1-(S)-methyl-2-methoxyethylamino)pyrimidin-4-yl]-6,7-dihydro-5H-pyrazolo[1,2-a]pyrazol-1-one];

Spiro[1,3-dioxolane[2',6]-2-(4-fluorophenyl)-3-(2-phenoxy-pyrimidin-4-yl)-6,7-dihydro-5H-pyrazolo[1,2-a]pyrazol-1-one;

Spiro[1,3-dioxolane[2',6]-2-(4-fluorophenyl)-3-[(2-fluoro-phenoxy)pyrimidin-4-yl]-6,7-dihydro-5H-pyrazolo[1,2-a]pyrazol-1-one];

Spiro[1,3-dioxane[2',6]-2-(4-fluorophenyl)-3-(2-phenoxy-pyrimidin-4-yl)-6,7-dihydro-5H-pyrazolo[1,2-a]pyrazol-1-one];

Spiro[1,3-dithiolane[2',6]-2-(4-fluorophenyl)-3-(2-phenoxy-pyrimidin-4-yl)-6,7-dihydro-5H-pyrazolo[1,2-a]pyrazol-1-one];

Spiro[1,3-dioxane[2',6]-2-(4-fluorophenyl)-3-[(2-(S)-(α)-methyl-benzylamino)pyrimidin-4yl]-6,7-dihydro-5H-pyrazolo[1,2-a]pyrazol-1-one];

Spiro[1,3-dioxane[2',6]-2-(4-fluorophenyl)-3-[2-(1,1-dimethylethylamino)pyrimidin-4-yl]-6,7-dihydro-5H-pyrazolo[1,2-a]pyrazol-1-one];

Spiro[1,3-dioxane[2',6]-2-(4-fluorophenyl)-3-[2-(benzylamino)pyrimidin-4-yl]-6,7-dihydro-5H-pyrazolo[1,2-a]pyrazol-1-one]; and Spiro[1,3-dioxane[2',6]-2-(4-fluorophenyl)-3-{2-[(2-methylphenyl)methylamino]pyrimidin-4-yl}-6,7-dihydro-5H-pyrazolo[1,2-a]pyrazol-1-one].

28. A pharmaceutical composition comprising:
a) an effective amount of one or more bicyclic pyrazolones including all enantiomeric and diasteriomeric forms and pharmaceutically acceptable salts thereof, said compound having the formula:

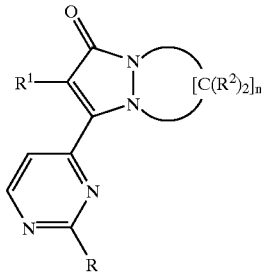

wherein R is:
a) —O[CH$_2$]$_k$R$^3$; or
b) —NR$^{4a}$R$^{4b}$;
   R$^3$ is substituted or unsubstituted C$_1$–C$_4$ alkyl, substituted or unsubstituted hydrocarbyl, substituted or unsubstituted heterocyclyl, substituted or unsubstituted aryl or alkylenearyl, substituted or unsubstituted heteroaryl or alkyleneheteroaryl; the index k is from 0 to 5;
   R$^{4a}$ and R$^{4b}$ are each independently:
     a) hydrogen; or
     b) —[C(R$^{5a}$R$^{5b}$)]$_m$R$^6$;
       each R$^{5a}$ and R$^{5b}$ are independently hydrogen, or C$_1$–C$_4$ linear, branched, or cyclic alkyl, and mixtures thereof; R$^6$ is —OR$^7$, —N(R$^7$)$_2$, —CO$_2$R$^7$, —CON(R$^7$)$_2$; substituted or unsubstituted C$_1$–C$_4$ alkyl, substituted or unsubstituted aryl, or substituted or unsubstituted heteroaryl; R$^7$ is hydrogen, a water-soluble cation, or C$_1$–C$_4$ alkyl; the index m is from 0 to 5;
R$^1$ is:
a) substituted or unsubstituted aryl; or
b) substituted or unsubstituted heteroaryl;
two R$^2$ units on the same carbon atom are taken together to form a spirocyclic ring having from 4 to 7 atoms, the balance of the R$^2$ units are independently selected from the group consisting of:
a) hydrogen;
b) —O(CH$_2$)$_j$R$^8$;
c) —(CH$_2$)$_j$NR$^{9a}$R$^{9b}$;
d) —CH$_2$)$_j$CO$_2$R$^{10}$;
e) —(CH$_2$)$_j$OCO$_2$R$^{10}$
f) —CH$_2$)$_j$CON(R$^{10}$)$_2$; and
g) two R$^2$ units can be taken together to form a carbonyl unit;
R$^8$, R$^{9a}$, R$^{9b}$, and R$^{10}$ are each independently hydrogen, C$_1$–C$_4$ alkyl, and mixtures thereof; R$^{9a}$ and R$^{9b}$ can be taken together to form a carbocyclic or heterocyclic ring comprising from 3 to 7 atoms; two R$^{10}$ units can be take together to form a carbocyclic or heterocyclic ring comprising from 3 to 7 atoms; j is an index from 0 to 5; the index n is from 3 to 5; and
b) one or more pharmaceutically acceptable excipients.

* * * * *

UNITED STATES PATENT AND TRADEMARK OFFICE
CERTIFICATE OF CORRECTION

PATENT NO. : 6,566,357 B1
DATED : May 20, 2003
INVENTOR(S) : Matthew John Laufersweiler et al.

It is certified that error appears in the above-identified patent and that said Letters Patent is hereby corrected as shown below:

Column 2,
Line 29, delete "$R^7$" and insert -- $OR^7$ --.

Signed and Sealed this

Fifth Day of April, 2005

JON W. DUDAS
*Director of the United States Patent and Trademark Office*